(12) United States Patent
Aoshima et al.

(10) Patent No.: US 10,709,406 B2
(45) Date of Patent: Jul. 14, 2020

(54) RADIOGRAPHY APPARATUS, METHOD FOR CONTROLLING RADIOGRAPHY APPARATUS, AND PROGRAM

(71) Applicant: FUJIFILM Corporation, Tokyo (JP)

(72) Inventors: Yuzo Aoshima, Kanagawa (JP);
Ryosuke Ogura, Kanagawa (JP);
Fumito Nariyuki, Kanagawa (JP);
Masayoshi Matsuura, Kanagawa (JP);
Haruyasu Nakatsugawa, Kanagawa (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 226 days.

(21) Appl. No.: 15/850,370

(22) Filed: Dec. 21, 2017

(65) Prior Publication Data

US 2018/0116524 A1    May 3, 2018

Related U.S. Application Data

(63) Continuation of application No. PCT/JP2016/003075, filed on Jun. 27, 2016.

(30) Foreign Application Priority Data

Jul. 7, 2015  (JP) .................................. 2015-135902

(51) Int. Cl.
*A61B 6/00*  (2006.01)
*A61B 6/12*  (2006.01)
(Continued)

(52) U.S. Cl.
CPC ............ *A61B 6/542* (2013.01); *A61B 5/0059* (2013.01); *A61B 6/06* (2013.01); *A61B 6/08* (2013.01);
(Continued)

(58) Field of Classification Search
CPC .... A61B 6/06; A61B 6/08; A61B 6/40; A61B 6/4064; A61B 6/4085; A61B 6/42;
(Continued)

(56) References Cited

U.S. PATENT DOCUMENTS 7,581,885 B2 *  9/2009  Ertel ........................ A61B 6/08
                                                     378/204
7,708,462 B2 *  5/2010  Fujiwara ................ A61B 6/025
                                                     378/206
(Continued)

FOREIGN PATENT DOCUMENTS

CN    102970929 A    3/2013
CN    107708569 A    2/2018
(Continued)

OTHER PUBLICATIONS

English translation of CN 107708569A by Patent Translate dated May 11, 2020.*
(Continued)

*Primary Examiner* — Allen C. Ho
(74) *Attorney, Agent, or Firm* — Sughrue Mion, PLLC

(57) ABSTRACT

A radiography apparatus includes a radiation emitting device that irradiates a subject with radiation, a camera that captures an image of the subject to acquire a captured image of the subject, and a radiation detector that detects the radiation transmitted through the subject and generates a radiographic image of the subject. The driving state of at least one of the radiation emitting device or the radiation detector is controlled on the basis of whether the radiation detector is included in the captured image.

21 Claims, 11 Drawing Sheets

(51) Int. Cl.
*A61B 6/06* (2006.01)
*A61B 6/08* (2006.01)
*A61B 5/00* (2006.01)

(52) U.S. Cl.
CPC ............... *A61B 6/12* (2013.01); *A61B 6/40* (2013.01); *A61B 6/4064* (2013.01); *A61B 6/4085* (2013.01); *A61B 6/42* (2013.01); *A61B 6/4208* (2013.01); *A61B 6/4233* (2013.01); *A61B 6/4258* (2013.01); *A61B 6/4283* (2013.01); *A61B 6/44* (2013.01); *A61B 6/4405* (2013.01); *A61B 6/4411* (2013.01); *A61B 6/4452* (2013.01); *A61B 6/46* (2013.01); *A61B 6/461* (2013.01); *A61B 6/462* (2013.01); *A61B 6/469* (2013.01); *A61B 6/52* (2013.01); *A61B 6/5211* (2013.01); *A61B 6/5229* (2013.01); *A61B 6/5247* (2013.01); *A61B 6/54* (2013.01); *A61B 6/545* (2013.01); *A61B 6/547* (2013.01); *A61B 6/58* (2013.01); *A61B 6/582* (2013.01); *A61B 6/583* (2013.01); *A61B 6/584* (2013.01); *A61B 6/585* (2013.01); *A61B 6/587* (2013.01); *A61B 6/588* (2013.01); *A61B 6/589* (2013.01); *A61B 6/544* (2013.01)

(58) Field of Classification Search
CPC ... A61B 6/4208; A61B 6/4233; A61B 6/4283; A61B 6/44; A61B 6/4405; A61B 6/4411; A61B 6/4452; A61B 6/46; A61B 6/461; A61B 6/462; A61B 6/469; A61B 6/52; A61B 6/5211; A61B 6/5229; A61B 6/5247; A61B 6/54; A61B 6/542; A61B 6/544; A61B 6/545; A61B 6/547; A61B 6/58; A61B 6/582; A61B 6/583; A61B 6/584; A61B 6/585; A61B 6/587; A61B 6/588; A61B 6/589
USPC ......... 378/62, 91, 98, 98.2, 98.3, 98.5, 98.8, 378/162, 165, 166, 189, 204–207
See application file for complete search history.

(56) References Cited

U.S. PATENT DOCUMENTS

| | | | | |
|---|---|---|---|---|
| 7,720,198 B2* | 5/2010 | Schliermann | ............ | A61B 6/08 378/108 |
| 7,726,879 B2* | 6/2010 | Abe | ............ | A61B 6/08 378/206 |
| 7,737,427 B2* | 6/2010 | Kito | ............ | A61B 6/4233 250/370.08 |
| 7,841,772 B2* | 11/2010 | Nishii | ............ | A61B 6/08 378/206 |
| 8,227,757 B2* | 7/2012 | Yokoyama | ............ | A61B 6/06 250/354.1 |
| 8,553,839 B2* | 10/2013 | Hendriks | ............ | A61B 6/4441 378/63 |
| 8,767,919 B2* | 7/2014 | Nishino | ............ | A61B 6/4007 378/108 |
| 8,867,702 B2* | 10/2014 | Nishino | ............ | A61B 6/4007 378/63 |
| 9,008,269 B2* | 4/2015 | Wang | ............ | A61B 6/52 378/146 |
| 9,028,144 B2* | 5/2015 | Choi | ............ | A61B 6/032 378/205 |
| 9,149,247 B2* | 10/2015 | Lee | ............ | A61B 6/4452 |
| 9,241,682 B2* | 1/2016 | Aram | ............ | A61B 6/5241 |
| 9,462,985 B2* | 10/2016 | Hu | ............ | A61B 6/547 |
| 9,480,443 B2* | 11/2016 | Feuerlein | ............ | A61B 6/032 |
| 9,521,987 B2* | 12/2016 | Tajima | ............ | A61B 6/08 |
| 9,566,040 B2* | 2/2017 | Hu | ............ | A61B 6/5205 |
| 9,662,086 B2* | 5/2017 | Ohta | ............ | A61B 5/0059 |
| 9,730,669 B2* | 8/2017 | Lee | ............ | A61B 6/545 |
| 9,799,114 B2* | 10/2017 | Piron | ............ | A61B 6/032 |
| 9,811,902 B2* | 11/2017 | Flohr | ............ | G06K 9/4604 |
| 9,820,705 B2* | 11/2017 | Kim | ............ | A61B 6/08 |
| 9,931,089 B2* | 4/2018 | Nariyuki | ............ | A61B 6/107 |
| 9,936,879 B2* | 4/2018 | Piron | ............ | A61B 5/055 |
| 9,949,699 B2* | 4/2018 | Visser | ............ | G06T 11/003 |
| 9,955,927 B2* | 5/2018 | Hendriks | ............ | A61B 6/025 |
| 9,968,502 B2* | 5/2018 | Hight | ............ | A61B 6/0407 |
| 9,974,504 B2* | 5/2018 | Lee | ............ | A61B 6/462 |
| 10,004,465 B2* | 6/2018 | Krauss | ............ | A61B 6/032 |
| 10,034,649 B2* | 7/2018 | Kim | ............ | A61B 6/544 |
| 10,039,509 B2* | 8/2018 | Okusu | ............ | A61B 6/4208 |
| 10,045,751 B2* | 8/2018 | Okusu | ............ | A61B 6/563 |
| 10,098,598 B2* | 10/2018 | Lee | ............ | A61B 6/465 |
| 10,143,428 B2* | 12/2018 | Eun | ............ | A61B 6/04 |
| 10,172,574 B2* | 1/2019 | Schäfer | ............ | A61B 6/02 |
| 10,181,074 B2* | 1/2019 | Braun | ............ | A61B 6/0457 |
| 10,188,365 B2* | 1/2019 | Lee | ............ | A61B 6/40 |
| 10,194,882 B2* | 2/2019 | Kwak | ............ | A61B 6/54 |
| 10,195,002 B2* | 2/2019 | Kim | ............ | G06T 19/00 |
| 10,213,169 B2* | 2/2019 | Braun | ............ | A61B 6/467 |
| 10,285,656 B2* | 5/2019 | Wang | ............ | A61B 6/4405 |
| 10,307,119 B2* | 6/2019 | Lim | ............ | A61B 6/10 |
| 10,376,217 B2* | 8/2019 | Schmidt | ............ | A61B 6/035 |
| 2006/0109958 A1 | 5/2006 | Ertel et al. | | |
| 2009/0136000 A1 | 5/2009 | Nishii et al. | | |
| 2011/0049370 A1 | 3/2011 | Yoshida et al. | | |
| 2011/0110497 A1 | 5/2011 | Nishino et al. | | |
| 2013/0114793 A1 | 5/2013 | Ohta et al. | | |
| 2013/0200842 A1 | 8/2013 | Takahashi | | |
| 2013/0272502 A1 | 10/2013 | Watanabe et al. | | |
| 2015/0055753 A1 | 2/2015 | Tajima | | |
| 2018/0116623 A1* | 5/2018 | Inoue | ............ | A61B 6/40 |

FOREIGN PATENT DOCUMENTS

| | | |
|---|---|---|
| EP | 3 331 749 A1 | 4/2018 |
| JP | 2007-29353 A | 2/2007 |
| JP | 2009-131323 A | 6/2009 |
| JP | 2010-119485 A | 6/2010 |
| JP | 2011-24721 A | 2/2011 |
| JP | 2011-45439 A | 3/2011 |
| JP | 2011-115566 A | 6/2011 |
| JP | 2012-29889 A | 2/2012 |
| JP | 2013-158589 A | 8/2013 |
| JP | 2013-220218 A | 10/2013 |

OTHER PUBLICATIONS

Communication dated May 15, 2018 from the European Patent Office in counterpart Application No. 16821013.6.
Portable X-ray Equipment, IPF-21, Toshiba Medical Supply Co., Ltd., Radiography Apparatus, Searched on Jul. 30, 1999, <URL: http://www.toshiba-irvouyouhin.co.ip/tmeds/xrays/ipf21.html> (4 pages total).
International Search Report dated Nov. 1, 2016 issued by the International Searching Authority in International Application PCT/JP2016/003075.
International Preliminary Report on Patentability dated Jan. 9, 2018, issued by the International Bureau in International Application PCT/JP2016/003075.
Written Opinion dated Nov. 1, 2016 issued by the International Searching Authority in International Application PCT/JP2016/003075.
Communication dated Apr. 7, 2020, from The State Intellectual Property Office of the P.R. of China in Application No. 201680036975.7.

* cited by examiner

RADIOGRAPHY APPARATUS, METHOD FOR CONTROLLING RADIOGRAPHY APPARATUS, AND PROGRAM

CROSS REFERENCE TO RELATED APPLICATIONS

The present application is a Continuation of PCT International Application No. PCT/JP2016/003075 filed on Jun. 27, 2016, which claims priority under 35 U.S.C. § 119(a) to Japanese Patent Application No. 2015-135902 filed on Jul. 7, 2015. Each of the above applications is hereby expressly incorporated by reference, in its entirety, into the present application.

BACKGROUND

Technical Filed

The present invention relates to a radiography apparatus that captures a radiographic image of a subject, a method for controlling the radiography apparatus, and a program.

Background Art

For example, as disclosed in JP2012-29889A and Toshiba Medical Supply Co., Ltd., Radiography Apparatus IPF-21, [online], [Searched on Jul. 30, 1999], Internet <URL: http://www.toshiba-iryouyouhin.co.jp/tmeds/xrays/ipf21.html>, a portable radiation emitting device has been proposed which is provided with only a minimum number of components for emitting radiation, such as a radiation source and an electric circuit, and can be operated by an operator while being held in the hand. This type of portable radiation emitting device is light enough to be operated by the operator while being held in the hand and is advantageous in capturing an image of an object in various directions.

In a case in which a radiographic image of a subject is captured by using the radiation emitting device, a radiation detector (a so-called "flat panel detector") that records a radiographic image indicating the subject using radiation that has been emitted and transmitted through the subject is generally used. As the radiation detector, a cassette-type radiation detector has been known in which, for example, an image detection unit, a battery for driving, and a control unit, such as an electric circuit related to driving, are accommodated in a housing. The radiation detector is located so as to face the radiation emitting device, with a subject interposed therebetween. In this state, the radiation emitting device is driven. Then, radiation transmitted through the subject is emitted to the radiation detector and a radiographic image indicated by the radiation transmitted through the subject is acquired.

The above-mentioned portable radiation emitting device can be operated by the operator while being held in the hand. However, a radiation emitting device including a support device that supports a radiation source unit including a radiation source has been proposed in order to prevent hand shaking and the exposure of, for example, the hand of the operator to radiation. Toshiba Medical Supply Co., Ltd., Radiography Apparatus IPF-21, [online], [Searched on Jul. 30, 1999], Internet <URL: http://www.toshiba-iryouyouhin.co.jp/tmeds/xrays/ipf21.html> discloses an example of the support device and particularly discloses a support device which includes a wheel portion provided in a lower part of a support leg and is movable.

A radiation emitting device including the support device basically includes a leg portion that is movable by a wheel, a main body portion that includes a battery for driving a radiation source and an electric circuit related to the driving of the radiation source and is held on the leg portion, and an arm portion that is connected to the main body portion. The radiation source unit is attached to a leading end of the arm portion.

In a case in which the radiation emitting device is used, first, the radiation emitting device is moved close to the bed on which a patient lies. Then, the radiation source unit is moved to a desired position and the radiation detector is moved to a desired position behind the back of the subject. In this state, the radiation source unit is driven to emit radiation to the subject and the radiation detector detects radiation transmitted through the subject and acquires a radiographic image of the subject.

In addition, a method has been proposed which captures an image of a subject with a camera to acquire a captured image indicating the surface of the subject and displays the captured image in order to, for example, recognize a radiation field in a radiography apparatus in which a radiation emitting device and a radiation detector are separately provided (see JP2009-131323A, JP2007-029353A, and JP2010-119485A). In addition, in the radiography apparatus in which the radiation emitting device and the radiation detector are separately provided, the deviation between the radiation field and a detection range of the radiation detector is likely to occur. Therefore, JP2009-13133A, JP2007-029353A, and JP2010-119485A also disclose a method which displays a frame indicating the radiation field and a frame indicating the detection region of the radiation detector so as to be superimposed on the displayed captured image.

SUMMARY OF THE INVENTION

The radiation emitting device having the above-mentioned configuration has the advantage that it can be moved in a narrow space or it can be used even in an environment in which an alternating current source is not available. Therefore, in particular, for example, the radiation emitting device is appropriately used to capture a radiographic image of the patient who is raced to a medical institution, such as a hospital, or the patient who lies on the bed in a narrow hospital room. The size and weight of the radiation emitting device are reduced in order to easily handle the radiation emitting device. Therefore, the size of a battery provided in the device is also reduced.

However, in a case in which the size of the battery is reduced, the capacity of the battery is also reduced. In particular, it is necessary to reduce the size of the battery in order to reduce the weight of the portable radiation emitting device for ease of handling. As a result, the capacity of the battery is further reduced. In addition, the size and capacity of the battery of the radiation detector are also reduced, considering ease of carrying a cassette. As such, the important task of the radiography apparatus including the radiation emitting device and the radiation detector which are provided with batteries with low capacity is to reduce power consumption.

The invention has been made in view of the above-mentioned problems and an object of the invention is to reduce power consumption in a radiography apparatus in which a radiation emitting device and a radiation detector are separately provided, a method for controlling the radiography apparatus, and a program.

A radiography apparatus according to the invention includes: a radiation emitting device that irradiates a subject with radiation; imaging unit for capturing an image of the subject to acquire a captured image of the subject; a radiation detector that detects the radiation transmitted through the subject and generates a radiographic image of the subject; and driving state control unit for controlling a driving state of at least one of the radiation emitting device or the radiation detector on the basis of whether the radiation detector is included in the captured image.

The "captured image of the subject" is an image indicating the surface of the subject and the surface of objects in the vicinity of the subject in an imaging range of the imaging unit. The captured image of the subject includes an infrared image which is acquired by capturing an image of the subject using infrared rays and indicates the temperature distribution of the surface of the subject and the surface of objects in the vicinity of the subject.

In the radiography apparatus according to the invention, in a case in which the radiation detector is included in the captured image, the driving state control unit may control the driving state of at least one of the radiation emitting device or the radiation detector such that power consumption is more than that in a case in which the radiation detector is not included in the captured image.

In the radiography apparatus according to the invention, in a case in which the state of the radiation detector changes from a state in which the radiation detector is not included in the captured image to a state in which the radiation detector is included in the captured image, the driving state control unit may change the driving state of the radiation detector from a power-off state to a power-on state.

In the radiography apparatus according to the invention, in a case in which the state of the radiation detector changes from a state in which the radiation detector is not included in the captured image to a state in which the radiation detector is included in the captured image, the driving state control unit may change the driving state of the radiation detector from a sleep state to a standby state.

In the radiography apparatus according to the invention, in the case in which the state of the radiation detector changes from the state in which the radiation detector is not included in the captured image to the state in which the radiation detector is included in the captured image, the driving state control unit may change the driving state of the radiation emitting device from a sleep state to a standby state.

The "power-off state" means a state in which power is not supplied to all components forming the radiation detector and the components are not driven. The "power-on state" means at least one of the sleep state, the standby state, or a state in which imaging is available which will be described below. The "sleep state" means a state in which, among components forming the radiation emitting device and the radiation detector, only components required for a process that is performed until the radiation detector is included in the captured image are driven. The "standby state" means a state in which, in addition to the components driven in the sleep state, components required for a process for preparation for imaging are driven. The "state in which imaging is available" means a state in which, in addition to the components driven in the standby state, components required for a process for immediately performing imaging are driven, that is, a state in which an imaging operation is performed to immediately emit radiation from the radiation emitting device and the radiation detector can detect radiation transmitted through the subject and immediately generate a radiographic image.

The radiography apparatus according to the invention may further include display unit for displaying the captured image.

The radiography apparatus according to the invention may further include display control unit for displaying at least one of identification information of the radiation detector, the driving state of the radiation detector, a vertical direction of the radiation detector, a remaining battery level of the radiation detector, a position of a center of the radiation detector in the case in which the radiation detector is included in the captured image, or a direction in which the radiation detector is present in the case in which the radiation detector is not included in the captured image so as to be superimposed on the captured image displayed on the display unit.

In a case in which, in a detection surface of the radiation detector, a predetermined side which is the top side and another side opposite to the predetermined side are defined, the "vertical direction of the radiation detector" means a direction from the opposite side to the predetermined side along a straight line perpendicular to the predetermined side and the opposite side.

The radiography apparatus according to the invention may further include radiation field control unit for controlling a field of the radiation emitted to the subject. The display control unit may display the captured image such that a region corresponding to the radiation field is identifiable, according to the driving state of at least one of the radiation emitting device or the radiation detector.

The term "identifiable" means that the region corresponding to the radiation field is distinguished in the captured image such that the region corresponding to the radiation field is clearly recognized. For example, the region corresponding to the radiation field is changed to a predetermined color or a frame is given to the region corresponding to the radiation field such that the region corresponding to the radiation field can be identified.

In the radiography apparatus according to the invention, in a case in which the driving state of at least one of the radiation emitting device or the radiation detector is changed to a driving state in which power consumption is more than that in a state in which the radiographic image is not included in the captured image, the display control unit may display the region corresponding to the radiation field so as to be superimposed on the captured image.

In the radiography apparatus according to the invention, the display control unit may display the region corresponding to the radiation field with a size corresponding to a source image receptor distance and a body thickness of the subject so as to be superimposed on the captured image.

The "source image receptor distance" means a distance between the position where radiation is emitted from the radiation source and the detection surface of the radiation detector.

The radiography apparatus according to the invention may further include input unit for receiving a command to change at least one of a position or a size of the region corresponding to the radiation field displayed on the display unit. The radiation field control unit may change the radiation field in response to the change command.

In the radiography apparatus according to the invention, the radiation field control unit may change the radiation field in response to a decision on the issuing of the change command.

In the radiography apparatus according to the invention, the driving state control unit may change the driving state of at least of the radiation emitting device or the radiation detector to a state in Which imaging is available in response to the radiation field change operation of the radiation field control unit.

In the radiography apparatus according to the invention, the radiation field control unit may change the radiation field such that the radiation field is matched with a range of the radiation detector.

The radiography apparatus according to the invention may further include: a visible light source that emits visible light to a range of the radiation field in response to an imaging operation; and switching unit for switching the turn-on and turn-off of the visible light source by the imaging operation.

In this case, the switching unit may switch the turn-on and turn-off of the visible light source according to a part of the subject included in the captured image.

The "imaging operation" means an operation for irradiating the subject with radiation. For example, an operation of pressing an imaging button for performing imaging corresponds to the imaging operation. In a case in which the imaging button is used to perform the imaging operation, the radiation emitting device can be configured as follows. The imaging button can be operated in two stages. That is, the imaging button can be pressed halfway and fully. The imaging button is pressed halfway to emit visible light to the range of the radiation field and is pressed fully to irradiate the subject with radiation. In this case, the imaging operation may be the operation of pressing the imaging button halfway or the operation of pressing the imaging button fully.

In the radiography apparatus according to the invention, the driving state control unit may change a lighting state of the visible light source according to the driving state of at least one of the radiation emitting device or the radiation detector.

The term "changing the lighting state of the visible light source" means changing the lighting state of the visible light source such that the driving state of at least one of the radiation emitting device and the radiation detector is known. For example, at least one of the color, turn-on time, or blinking pattern of the visible light source is changed according to the driving state to change the lighting state of the visible light source.

In the radiography apparatus according to the invention, the captured image may be an infrared image and the display unit may display the infrared image and the radiographic image.

The radiography apparatus according to the invention may further include: movement amount detection unit for detecting an amount of movement of the radiation emitting device per unit time; and imaging allowance unit for allowing the emission of the radiation from the radiation emitting device in a case in which the amount of movement is less than a threshold value.

According to the invention, there is provided a method for controlling a radiography apparatus including a radiation emitting device that irradiates a subject with radiation, imaging unit for capturing an image of the subject to acquire a captured image of the subject, and a radiation detector that detects the radiation transmitted through the subject and generates a radiographic image of the subject. The method includes controlling a driving state of at least one of the radiation emitting device or the radiation detector on the basis of whether the radiation detector is included in the captured image.

In addition, a program that causes a computer to perform the method for controlling a radiography apparatus according to the invention may be provided.

According to the invention, the driving state of at least one of the radiation emitting device or the radiation detector is controlled on the basis of whether the radiation detector is included in the captured image. Here, in a state in which the radiation detector is not included in the captured image, an image of the subject is not captured. After the radiation detector is included in the captured image, radiation is emitted to the subject to capture an image of the subject. Therefore, the configuration in which the driving state of at least one of the radiation emitting device or the radiation detector is controlled on the basis of whether the radiation detector is included in the captured image makes it possible to prevent at least one of the radiation emitting device or the radiation detector from being changed to the driving state in which power consumption is large in a situation in which imaging is not immediately performed. Therefore, it is possible to reduce the power consumption of the radiography apparatus according to the invention.

DESCRIPTION OF EMBODIMENTS

Figure 1:
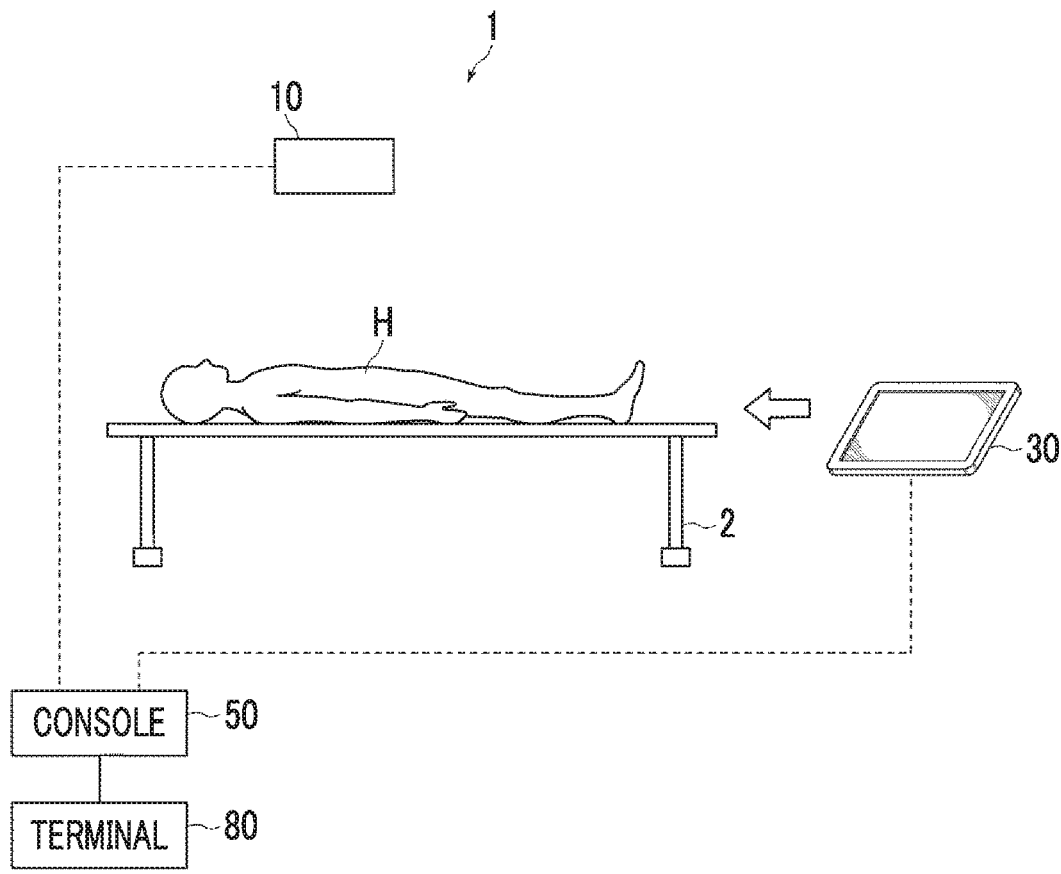
FIG. 1 is a diagram schematically illustrating a radiography apparatus according to an embodiment of the invention.

Hereinafter, embodiments of the invention will be described with reference to the drawings. FIG. 1 is a diagram schematically illustrating a radiography apparatus according to an embodiment of the invention. As illustrated in FIG. 1, a radiography apparatus 1 according to this embodiment includes a portable radiation emitting device 10, a radiation detector 30, and a console 50. For example, in order to acquire a radiographic image of a subject H that lies on a bed 2, the radiation detector 30 is inserted between the subject H and the bed 2, the subject H is irradiated with radiation emitted from the portable radiation emitting device 10, and a radiographic image of the subject H is acquired by the radiation detector 30. In addition, the console 50 is connected to a terminal 80 of, for example, a doctor through a network.

Figure 2:
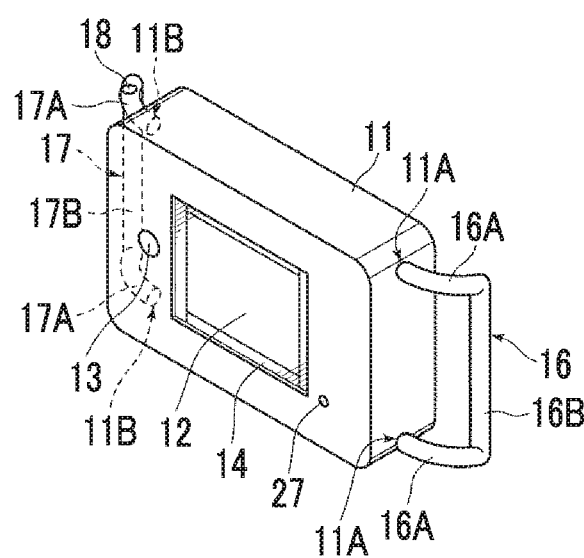
FIG. 2 is a front perspective view illustrating a radiation emitting device.
Figure 3:
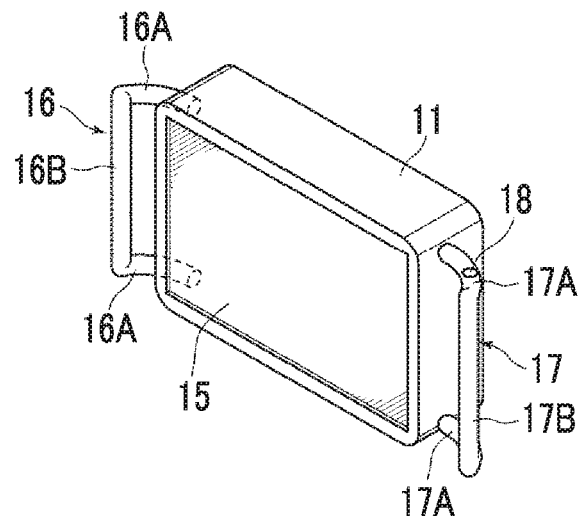
FIG. 3 is a rear perspective view illustrating the radiation emitting device.
Figure 4:
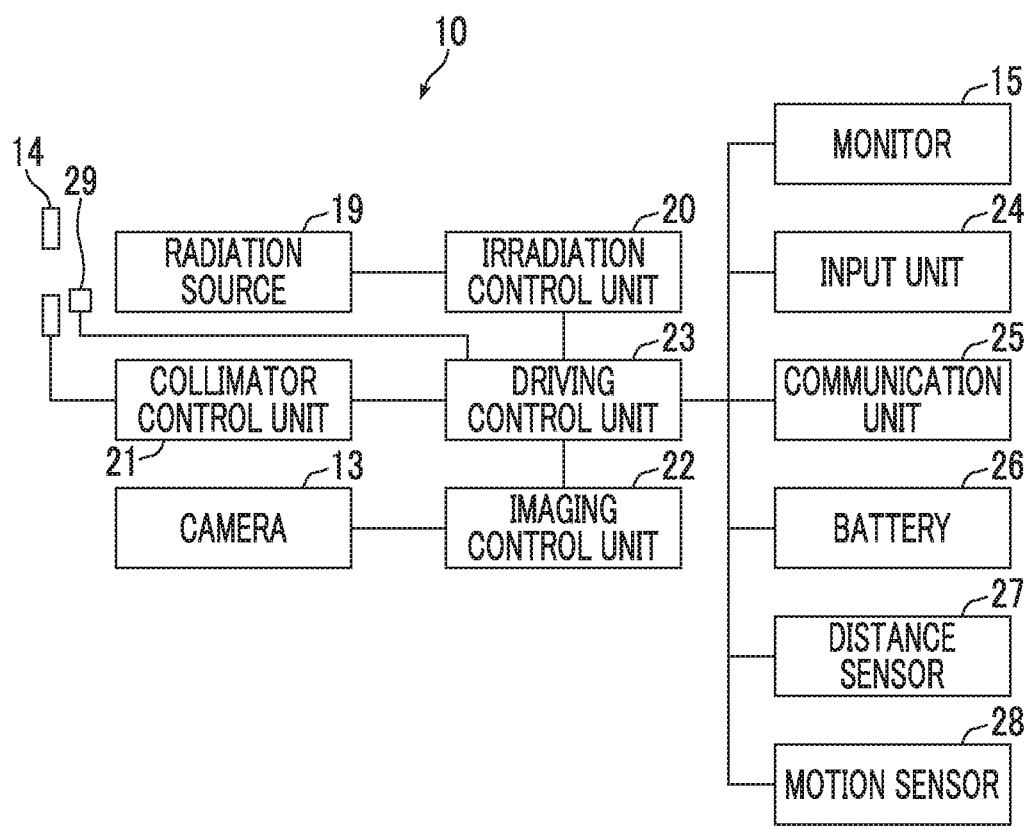
FIG. 4 is a block diagram schematically illustrating the internal configuration of the radiation emitting device.

FIG. 2 is a front perspective view illustrating the radiation emitting device. FIG. 3 is a rear perspective view illustrating the portable radiation emitting device 10. FIG. 4 is a block diagram schematically illustrating the internal configuration of the portable radiation emitting device 10. As illustrated in the drawings, in the portable radiation emitting device 10, an emission window 12 through which radiation is emitted, a camera 13 that captures an image of the surface of the subject H, and a distance sensor 27 are provided on a front surface of a housing 11 with a rectangular parallelepiped shape. A collimator 14 for narrowing the emission range of radiation is seen from the emission window 12. A monitor 15, such as a liquid crystal display unit, is provided on a rear surface of the housing 11. For example, a captured image acquired by capturing the image of the surface of the subject H using the camera 13, a radiographic image of the subject H, and various kinds of information for setting the portable radiation emitting device 10 are displayed on the monitor 15. The distance sensor 27 measures the distance between the portable radiation emitting device 10 and a target object, using a laser or ultrasonic waves. In addition, the camera 13 and the monitor 15 correspond to imaging unit and display unit, respectively.

Holding portions 16 and 17 are attached to both side surfaces of the housing 11. The holding portion 16 includes two protruding portions 16A that protrude from the upper and lower portions of the side surface of the housing 11 to the side and a connection portion 16B that connects the two protruding portions 16A. The holding portion 17 includes two protruding portions 17A that protrude from the upper and lower portions of the side surface of the housing 11 to the side and a connection portion 17B that connects the two protruding portions 17A. The protruding portions 16A and 17A are curved from protruding positions 11A and 11B to the rear surface of the housing 11. The protruding portions 16A and 17A may be inclined from the protruding positions 11A and 11B to the rear surface of the housing 11, instead of being curved. An operator can hold the holding portions 16 and 17 and move the portable radiation emitting device 10 to a position where an image of the subject H can be captured. In addition, an imaging button 18 for emitting radiation to capture an image of the subject H is provided in the upper protruding portion 17A of the holding portion 17 that is held by the right hand in a case in which the operator performs an imaging operation.

The housing 11 includes the monitor 15, a radiation source 19, an irradiation control unit 20, a collimator control unit 21, an imaging control unit 22, a driving control unit 23, an input unit 24, a communication unit 25, a battery 26, a distance sensor 27, a motion sensor 28, and a radiation field lamp 29. The irradiation control unit 20, the collimator control unit 21, the imaging control unit 22, the driving control unit 23, and the communication unit 25 are implemented by a program (software) that is operated in a computer, dedicated hardware, or a combination thereof. The program is recorded on a recording medium, such as a digital versatile disc (DVD) or a compact disk read only memory (CD-ROM), and is then distributed. The program is installed in the portable radiation emitting device 10 from the recording medium. Alternatively, the program is stored in a storage device of a server computer that is connected to a network or a network storage such that it can be accessed from the outside. The program is downloaded and installed in the portable radiation emitting device 10, if necessary.

The radiation source 19 includes, for example, an X-ray tube, a booster circuit, and cooling means for cooling the X-ray tube.

The irradiation control unit 20 drives the radiation source 19 and controls the amount of radiation emitted to the subject H such that radiation with intensity corresponding to predetermined imaging conditions is emitted to the subject H for only a set period of time. The imaging conditions include a tube voltage (kV value) and an mAs value (a tube current×an irradiation time) corresponding to the body thickness of the subject H. The body thickness of the subject H can be calculated by measuring a source image receptor distance (SID) which is the distance between the device 10 and the surface of the radiation detector 30 and a source object distance (SOD) which is the distance between the device 10 and the surface of the subject H, using the distance sensor 27, and subtracting the SOD from the SID. In addition, the operator may measure the body thickness and input information for setting the imaging conditions including the measured body thickness to the device 10 through the input unit 24. In this embodiment, the information for setting the imaging conditions including, for example, the body thickness is transmitted to the console 50 and the imaging conditions are set in the console 50. The set imaging conditions are transmitted to the radiation emitting device 10. The irradiation control unit 20 controls the emission of radiation to the subject H, using the imaging conditions transmitted from the console 50.

The collimator control unit 21 includes, for example, a driving mechanism, such as a motor for driving the collimator 14 to change the field of the radiation emitted from the radiation source 19 to the subject H, and an electric circuit for controlling the driving mechanism. The collimator control unit 21 controls the driving of the collimator 14 in response to a command from the driving control unit 23. The collimator control unit 21 corresponds to radiation field control unit.

The imaging control unit 22 drives the camera 13 to capture an image of the surface of the subject H and acquires a captured image G1. In addition, the imaging control unit 22 may perform image processing for improving image quality for the captured image G1 acquired by the camera 13. The captured image G1 acquired by the camera 13 is a motion picture with a predetermined frame rate of, for example, 30 fps.

The driving control unit 23 controls the overall driving operation of the radiation emitting device 10. That is, the driving control unit 23 performs, for example, a process of instructing the irradiation control unit 20 to drive the radiation source 19, a process of instructing the collimator control unit 21 to drive the collimator 14, a process of instructing the imaging control unit 22 to drive the camera 13 such that the captured image G1 is acquired, a process of displaying various kinds of information including the captured image G1 on the monitor 15, a process of instructing the communication unit 25 to exchange various kinds of information with the console 50, a process of monitoring the state of the battery 26, a process of receiving a command from the input unit 24, a process of measuring the distance between the radiation emitting device 10 and an object using the distance sensor 27, a process of detecting the movement of the radiation emitting device 10 using the motion sensor 8, and a process of setting the driving state of the radiation emitting device 10. In addition, each of the above-mentioned processes is performed by the commands from the input unit 24 or the commands that have been transmitted from the console 50 and received by the communication unit 25. The driving control unit 23 corresponds to display control unit, switching unit, and imaging allowance unit.

The input unit 24 is a touch-panel-type input unit that is integrated with the monitor 15, receives a command from the operator, and outputs information indicating the command to the driving control unit 23. It is assumed that the imaging button 18 is also included in the input unit 24.

The communication unit 25 performs wireless communication with the console 50 to exchange information. Examples of the information transmitted from the communication unit 25 to the console 50 include the captured image G1, the SID and the SOD measured by the distance sensor 27, the information of the radiation field defined by the collimator 14, movement information detected by the motion sensor 28 which will be described below, and information for setting the imaging conditions set by the operator through the input unit 24. Examples of the information transmitted from the console 50 to the communication unit 25 include a command to change the driving state of the radiation emitting device 10 and information such as imaging conditions. In addition, the radiation emitting device 10 may be connected to the console 50 by a cable, instead of wireless communication, and may exchange information with the console 50 in a wired manner. In the latter case, the communication unit 25 has a connector to which the cable is connected.

The motion sensor 28 is a 9-axis motion sensor that detects 3-axis acceleration, 3-axis angular velocity, and 3-axis tilt. The acceleration, angular velocity, and tilt detected by the motion sensor 28 are output as movement information to the driving control unit 23, are used to control the radiation emitting device 10 during imaging, and are transmitted from the communication unit 25 to the console 50. Here, the term "tilt" means a tilt with respect to the position where the radiation emitting device 10 is kept horizontal in a state in which a radiation emission axis, which is an axis aligned with the emission direction of radiation, is aligned with the direction of gravity. The motion sensor 28 corresponds to movement amount detection unit.

The radiation field lamp 29 is a light emitting element such as a light bulb or a light emitting diode (LED) that emits visible light. The driving control unit 23 controls the turn-on and turn-off of the radiation field lamp 29. When the radiation field lamp 29 is turned on, visible light is emitted to the radiation field in which radiation is emitted on the subject H. The radiation field lamp 29 corresponds to a visible light source.

Figure 5:
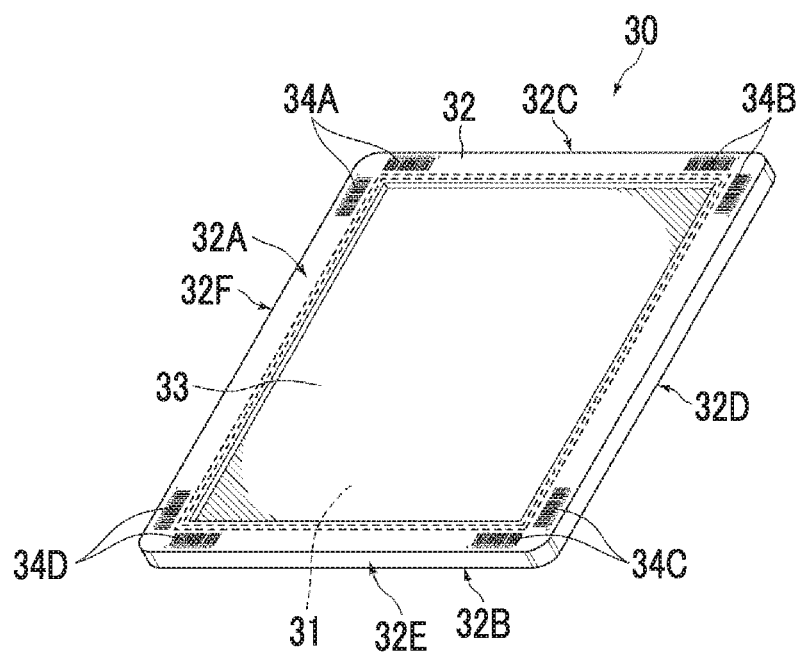
FIG. 5 is a perspective view illustrating the outward appearance of a radiation detector as viewed from a front surface which is a radiation emitting side.
Figure 6:
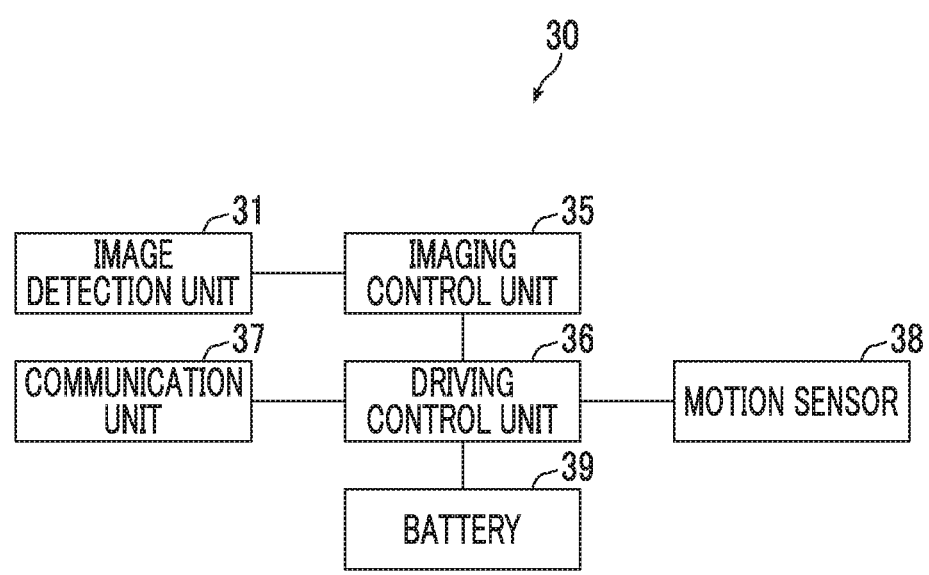
FIG. 6 is a block diagram schematically illustrating the internal configuration of the radiation detector.

Next, the configuration of the radiation detector 30 will be described. FIG. 5 is a perspective view illustrating the outward appearance of the radiation detector as viewed from the front side which is a radiation emitting side and FIG. 6 is a block diagram schematically illustrating the internal configuration of the radiation detector.

As illustrated in FIG. 5, the radiation detector 30 is a cassette-type radiation detector including a housing 32 that accommodates an image detection unit 31. The image detection unit 31 includes a scintillator (phosphor) that converts incident radiation into visible light and a thin film transistor (TFT) active matrix substrate, as known in the art. A rectangular imaging region in which a plurality of pixels that accumulate charge corresponding to the visible light from the scintillator are arranged is formed on the TFT active matrix substrate. The housing 32 includes, for example, an imaging control unit 35 including a gate driver that applies a gate pulse to a gate of a TFT to switch the TFT and a signal processing circuit that converts the charge accumulated in the pixel into an analog electric signal indicating an X-ray image and outputs the analog electric signal, in addition to the image detection unit 31.

The housing 32 has a rectangular parallelepiped shape having a front surface 32A on which radiation is incident, a rear surface 32B opposite to the front surface 32A, and four side surfaces 32C, 32D, 32E, and 32F. The housing 32 is made of, for example, a conductive resin and also functions as an electromagnetic shield that prevents the penetration of electromagnetic noise into the radiation detector 30 and the emission of electromagnetic noise from the inside of the radiation detector 30 to the outside. The housing 32 has a size that is based on International Organization for Standardization (ISO) 4090:2001 and is substantially equal to the size of, for example, a film cassette, an imaging plate (IP) cassette, or a computed radiography (CR) cassette.

A transmission plate 33 that transmits radiation is attached to the front surface 32A of the housing 32. The transmission plate 33 has a size that is substantially equal to the size of a radiation detection region of the radiation detector 30 and is made of a carbon material that has a small weight, high rigidity, and high transmittance.

Markers 34A to 34D that indicate identification information for identifying the radiation detector 30 are attached to four corners of the front surface 32A of the housing 32. In this embodiment, each of the markers 34A to 34D includes two bar codes that are perpendicular to each other. The two bar codes are attached to the front surface 32A of the radiation detector 30 so as to define four corners of the detection region of the radiation detector 30. For example, a tape with a color unique to the radiation detector 30 may be used as the marker as long as it can identify the radiation detector 30. In this case, it is possible to identify the radiation detector 30 with the colors of the markers.

Here, each of the markers 34A to 34D is a pair of two bar codes. However, in this embodiment, information indicating the vertical direction of the image detection unit 31 provided in the radiation detector 30 is included in one of the two bar codes. In this embodiment, the side to which the markers 34A and 34B are attached is an upper side, that is, a top side. Therefore, in this embodiment, in the radiation detector 30, in a case in which the side to which the markers 34A and 34B are attached and the side to which the markers 34C and 34D are attached are defined, a direction from the side to which the markers 34A and 34B are attached to the side to which the markers 34C and 34D are attached along a straight line perpendicular to the two sides is the vertical direction. The vertical direction means a direction on the radiation detector 30 and does not mean the direction of gravity.

In addition, a light emitting element, such as an LED that emits light with a color unique to the radiation detector 30, may be used as the marker. In this case, the radiation detector 30 can be identified by the color of the light emitting element. In addition, in a case in which a plurality of light emitting elements are used, the radiation detector 30 can be identified by the turn-on pattern or the blinking pattern of the light emitting elements.

The housing 32 includes the image detection unit 31, the imaging control unit 35, a driving control unit 36, a communication unit 37, a motion sensor 38, and a battery 39. The imaging control unit 35, the driving control unit 36, and the communication unit 37 are implemented by a program (software) that is operated in a computer, dedicated hardware, or a combination thereof. The program is installed in the radiation detector 30 as in the radiation emitting device 10.

As described above, the imaging control unit 35 includes, for example, the gate driver and the signal processing circuit, controls the driving of the gate driver and the signal processing circuit such that an analog image signal indicating a radiographic image G2 is generated and outputs the analog image signal to the driving control unit 36.

The driving control unit 36 controls the overall driving operation of the radiation detector 30. That is, the driving control unit 36 performs, for example, a process of instructing the imaging control unit 35 to generate an image signal indicating the radiographic image G2, a process of instructing the communication unit 37 to exchange the image signal indicating the radiographic image G2 and various kinds of information with the console 50, a process of detecting the movement of the radiation detector 30 using the motion sensor 38, a process of monitoring the state of the battery 39, and a process of setting the driving state of the radiation detector 30.

The communication unit 37 performs wireless communication with the console 50 to exchange information. Examples of the information transmitted from the communication unit 37 to the console 50 include the image signal indicating the radiographic image G2, movement information detected by the motion sensor 38 which will be described below, information indicating the current driving state of the radiation detector 30, and information indicating the remaining level of the battery 39. An example of the information transmitted from the console 50 to the communication unit 37 is information, such as a command to change the driving state of the radiation detector 30. In addition, the radiation detector 30 may be connected to the console 50 by a cable, instead of wireless communication, and may exchange information with the console 50 in a wired manner. In the latter case, the communication unit 37 has a connector to which the cable is connected.

The motion sensor 38 is a 9-axis motion sensor that detects 3-axis acceleration, 3-axis angular velocity, and 3-axis tilt. The acceleration, angular velocity, and tilt detected by the motion sensor 38 are output as movement information to the driving control unit 36 and are transmitted from the communication unit 37 to the console 50. The term "tilt" means a tilt with respect to the position where the radiation detector 30 is kept horizontal.

Figure 7:
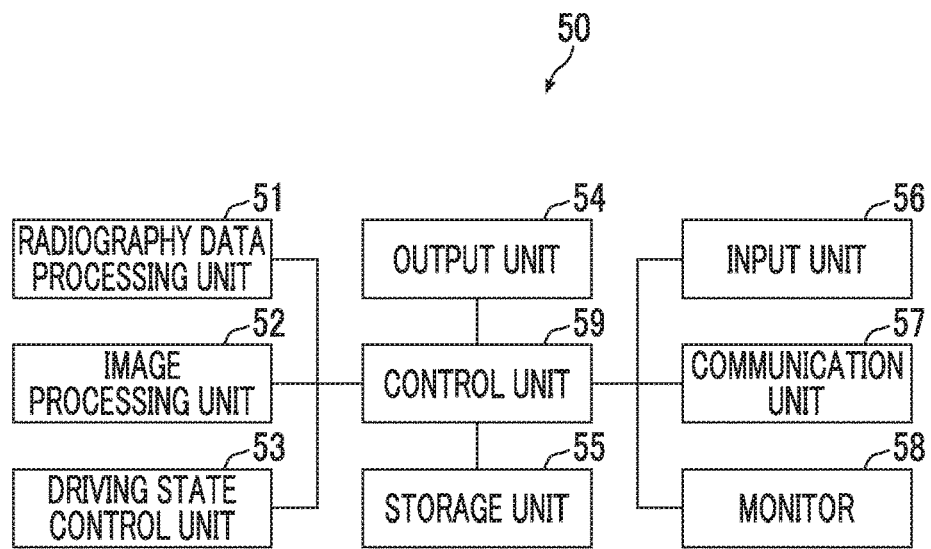
FIG. 7 is a block diagram schematically illustrating the internal configuration of a console.

FIG. 7 is a block diagram schematically illustrating the internal configuration of the console. As illustrated in FIG. 7, the console 50 includes a radiography data processing unit 51, an image processing unit 52, a driving state control unit 53, an output unit 54, a storage unit 55, an input unit 56, a communication unit 57, a monitor 58, and a control unit 59. The radiography data processing unit 51, the image processing unit 52, the driving state control unit 53, the communication unit 57, and the control unit 59 are implemented by a program (software) that is operated in a computer, dedicated hardware, or a combination thereof. The program is installed in the console 50 as in the radiation emitting device 10.

The radiography data processing unit 51 performs data processing, such as A/D conversion, for the image signal indicating the radiographic image G2 of the subject H which has been input from the radiation detector 30. The radiography data processing unit 51 outputs radiographic image data indicating the digital radiographic image G2 subjected to the data processing.

The image processing unit 52 performs predetermined image processing for the radiographic image data output from the radiography data processing unit 51, using image processing parameters stored in the storage unit 55. Examples of the image processing performed by the image processing unit 52 include various types of image processing, such as image calibration (the correction of radiographic image data by calibration data) including pixel defect correction, a process of creating a defect map for performing the pixel defect correction, offset correction, gain correction using a predetermined uniformly exposed image, and shading correction, a gradation correction process, a density correction process, a process of removing scattered rays caused by radiation transmitted through the subject H, and data conversion for converting image data into data for monitor display or data for printout. The image processing unit 52 outputs radiographic image data subjected to the image processing.

In the related art, in a case in which a radiographic image of a subject is captured, a scattered ray removal grid (hereinafter, simply referred to as a grid) is provided between the subject and a radiation detector and imaging is performed, in order to solve the problem that the contrast of the radiographic image is reduced by the scattering of radiation in the subject. In a case in which imaging is performed using the grid, radiation scattered by the subject is less likely to be emitted to the radiation detector, which makes it possible to improve the contrast of the radiographic image. However, for example, the grid is formed by alternately arranging lead that does not transmit radiation and an interspace material, such as aluminum or fiber that is likely to transmit radiation, at a small grating density of about 4.0 lines/mm and is heavy. Therefore, during imaging in, for example, a hospital, it is necessary to put the heavy grid between the patient who lies on the bed and the radiation detector. As a result, a burden on the placement operation and a burden on the patient during imaging increase. In addition, in the case of a convergence-type grid, there is a concern that density unevenness will occur in a radiographic image due to the oblique incidence of radiation. Furthermore, there is a concern that both the image of the subject and moire which is a fine stripe pattern corresponding to the pitch between the grids will be recorded on the radiographic image and the radiographic image will be difficult to see.

For this reason, a method has been performed which captures a radiographic image, without using a grid, and gives the same effect of improving image quality as that obtained by removing scattered rays using a grid to the radiographic image using image processing (for example, U.S. Pat. No. 8,064,676B and "C Fivez et al., Multiresolution contrast amplification in digital radiography with compensation for scattered radiation, 1996 IEEE, pp. 339-342."). This method performs frequency decomposition to decompose a radiographic image into a plurality of frequency components, performs a scattering component removal process of removing contrast or latitude for a low-frequency component which is regarded as a component of a scattered ray, and combines the processed frequency components to acquire a radiographic image from which components of the scattered rays have been removed. The use of the method for removing the scattered rays using image processing makes it unnecessary to use a grid during imaging. Therefore, it is possible to reduce the burden on the patient during imaging and to prevent density unevenness and the degradation of image quality due to moire.

In the process of removing scattered rays from the radiographic image G2, the body thickness of the subject H and imaging conditions are used. Therefore, in this embodiment, the image processing unit 52 of the console 50 performs the scattered ray removal process, using the body thickness of the subject H measured by the radiation emitting device 10 and the imaging conditions calculated by the control unit 59 which will be described below.

The driving state control unit 53 determines whether the captured image G1 output from the radiation emitting device 10 includes the radiation detector 30 and controls the driving state of at least one of the radiation emitting device 10 or the radiation detector 30 on the basis of whether the captured image G1 includes the radiation detector 30. In this embodiment, it is assumed that the driving state control unit 53 controls the driving state of both the radiation emitting device 10 and the radiation detector 30.

Figure 8:
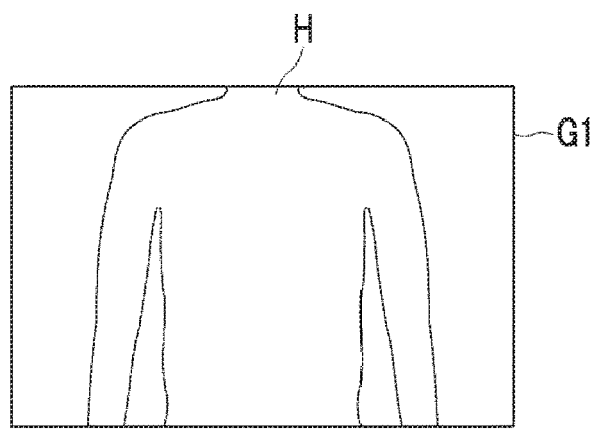
FIG. 8 is a diagram illustrating a captured image including only a subject.
Figure 9:
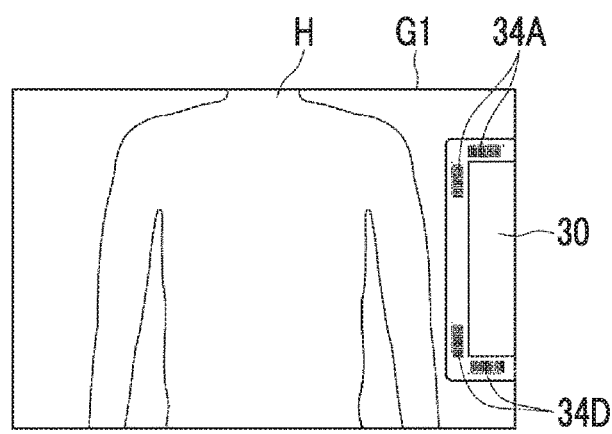
FIG. 9 is a diagram illustrating a captured image including a portion of the radiation detector in addition to the subject.

Next, the detection of the radiation detector 30 in the captured image G1 will be described. In a case in which a radiographic image of the subject H is acquired, the operator places the radiation emitting device 10 to face the subject H and takes the image of the subject H using the camera 13. In this embodiment, it is assumed that the image of the chest of the subject H is captured. Therefore, before imaging, the captured image G1 includes the chest of the subject H as illustrated in FIG. 8. Then, in a case in which an operation of inserting the radiation detector 30 between the bed 2 and the subject H is performed in order to acquire the radiographic image G2 of the subject H, the captured image G1 includes a portion of the radiation detector 30 as illustrated in FIG. 9. Here, the markers 34A to 34D are attached to four corners of the radiation detector 30. The driving state control unit 53 detects whether the captured image G1 includes any one of the markers 34A to 34D. In a case in which the captured image G1 includes any one of the markers 34A to 34D, the driving state control unit 53 determines that the captured image G1 includes the radiation detector 30.

The control unit 59 transmits radiation detector position information indicating the position of the radiation detector 30 in the captured image G1 from the communication unit 57 to the radiation emitting device 10. The radiation detector position information is a coordinate position indicating the position of the corners of the detection region of the radiation detector 30 on the captured image G1. In this embodiment, the size of the detection region of the radiation detector 30 is stored in the storage unit 55 in advance. The control unit 59 calculates the radiation detector position information from the position of any one of the markers 34A to 34D which has been detected from the captured image G1 by the driving state control unit 53 and the size of the detection region. In addition, in a case in which the radiation detector position information has been known, it is possible to calculate the information of the position of the center of the radiation detector 30 from the size of the detection region of the radiation detector 30. Therefore, the control unit 59 also transmits center position information indicating the position of the center of the radiation detector 30 to the radiation emitting device 10.

Here, the driving state of the radiation emitting device 10 includes a power-off state, a sleep state, a standby state, and a ready state. Here, the ready state corresponds to a state in which imaging is available. Power is turned on in the sleep state, the standby state, and the ready state. The power-off state is a state in which power is not supplied from the battery 26 to all of the components of the radiation emitting device 10. The sleep state is a state in which power is supplied to the driving control unit 23, the camera 13, the monitor 15, the imaging control unit 22, and the communication unit 25, the captured image G1 can be acquired, the captured image G1 can be displayed on the monitor 15, information for setting imaging conditions can be received from the input unit 24, and the communication unit 25 can exchange information with the console 50. The standby state is a state in which power is supplied to the irradiation control unit 20 and the collimator control unit 21, imaging conditions can be set, and the collimator 14 can be driven, in addition to the sleep state. The ready state is a state in which power is supplied to the radiation source 19 and the imaging button 18 can be operated to immediately emit radiation from the radiation source 19, in addition to the standby state. Therefore, the power-off state has the lowest power consumption, followed by the sleep state, the standby state, and the ready state.

The driving state of the radiation detector 30 includes a power-off state, a sleep state, and a standby state. Power is turned on in the sleep state and the standby state. The power-off state is a state in which power is not supplied from the battery 39 to all of the components of the radiation detector 30. The sleep state is a state in which power is supplied to the driving control unit 36, the communication unit 37, and the motion sensor 38, the communication unit 37 can exchange information with the console 50, and the motion sensor 38 can detect the movement of the radiation detector 30 and transmit movement information to the console 50. The standby state is a state in which power is supplied to the image detection unit 31 and the imaging control unit 35, in addition to the driving control unit 36 and the communication unit 37, radiation transmitted through the subject H can be detected, and a radiographic image indicating the subject H can be acquired. Therefore, the power-off state has the lowest power consumption, followed by the sleep state and the standby state.

The radiation detector 30 is turned on by the operator in a case in which it starts to be used on each day of use and is in the sleep state before imaging starts. The radiation emitting device 10 is turned on before a pre-imaging operation, which will be described below, starts and is in the sleep state.

In a case in which the radiation detector 30 is detected from the captured image G1, the driving state control unit 53 changes the driving state of the radiation emitting device 10 and the radiation detector 30 from the sleep state to the standby state. In addition, in a case in which the radiation field is set in the radiation emitting device 10 which will be described below, the driving state control unit 53 changes the driving state of the radiation emitting device 10 to the ready state. Therefore, the driving state control unit 53 outputs a command to change the driving state to the control unit 59. In a case in which the command is input, the control unit 59 transmits the command from the communication unit 57 to the radiation emitting device 10 and the radiation detector 30. In a case in which the command is received, the radiation emitting device 10 and the radiation detector 30 change the driving state in response to the command.

The output unit 54 outputs the radiographic image data subjected to the image processing which has been input from the image processing unit 52. The output unit 54 is, for example, a printer that prints out a radiographic image or a storage device that stores radiographic image data.

The storage unit 55 stores, for example, the size of the detection region of the radiation detector 30, image processing parameters for image processing performed by the image processing unit 52, parameters corresponding to the type of the radiation detector 30 and the body thickness of the subject H for setting the imaging conditions, and various kinds of information required for processes in the console 50. In addition, the storage unit 55 stores, for example, the radiographic image G2 output from the image processing unit 52 and the captured image G1 transmitted from the radiation emitting device 10. The storage unit 55 may be a semiconductor memory or a recording medium such as a hard disk. In addition, the storage unit 55 may be provided in the console 50. Alternatively, the storage unit 55 may be provided outside the console 50, may be connected to the console 50, and may be used.

The input unit 56 is, for example, a keyboard for inputting various kinds of information to the console 50. In addition, the input unit 56 may be a touch panel.

The communication unit 57 performs wireless communication with the radiation emitting device 10 and the radiation detector 30 to exchange information. In addition, the console 50 may be connected to the radiation emitting device 10 and the radiation detector 30 by a cable, instead of wireless communication, and exchange information with the radiation emitting device 10 and the radiation detector 30 in a wired manner. In the latter case, the communication unit 57 has a connector to which the cable is connected.

The monitor 58 is, for example, a liquid crystal panel and displays various kinds of information related to the console 50 and the radiographic image G2 transmitted from the radiation detector 30. In addition, the monitor 58 displays, for example, the captured image G1 if necessary.

The control unit 59 controls the overall driving operation of the console 50. That is, the control unit 59 performs, for example, a process of instructing the radiography data processing unit 51 to acquire the radiographic image G2, a process of instructing the image processing unit 52 to perform image processing for the radiographic image G2, a process of instructing the driving state control unit 53 to control the driving state of the radiation emitting device 10 and the radiation detector 30, a process of acquiring the identification information of the radiation detector 30 from any one of the markers 34A to 34D detected by the driving state control unit 53, a process of outputting the radiographic image G2 to the output unit 54, a process of instructing the communication unit 57 to exchange various kinds of information with the radiation emitting device 10 and the radiation detector 30, a process of receiving commands from the input unit 56, and a process of displaying various kinds of information on the monitor 58.

Figure 10:
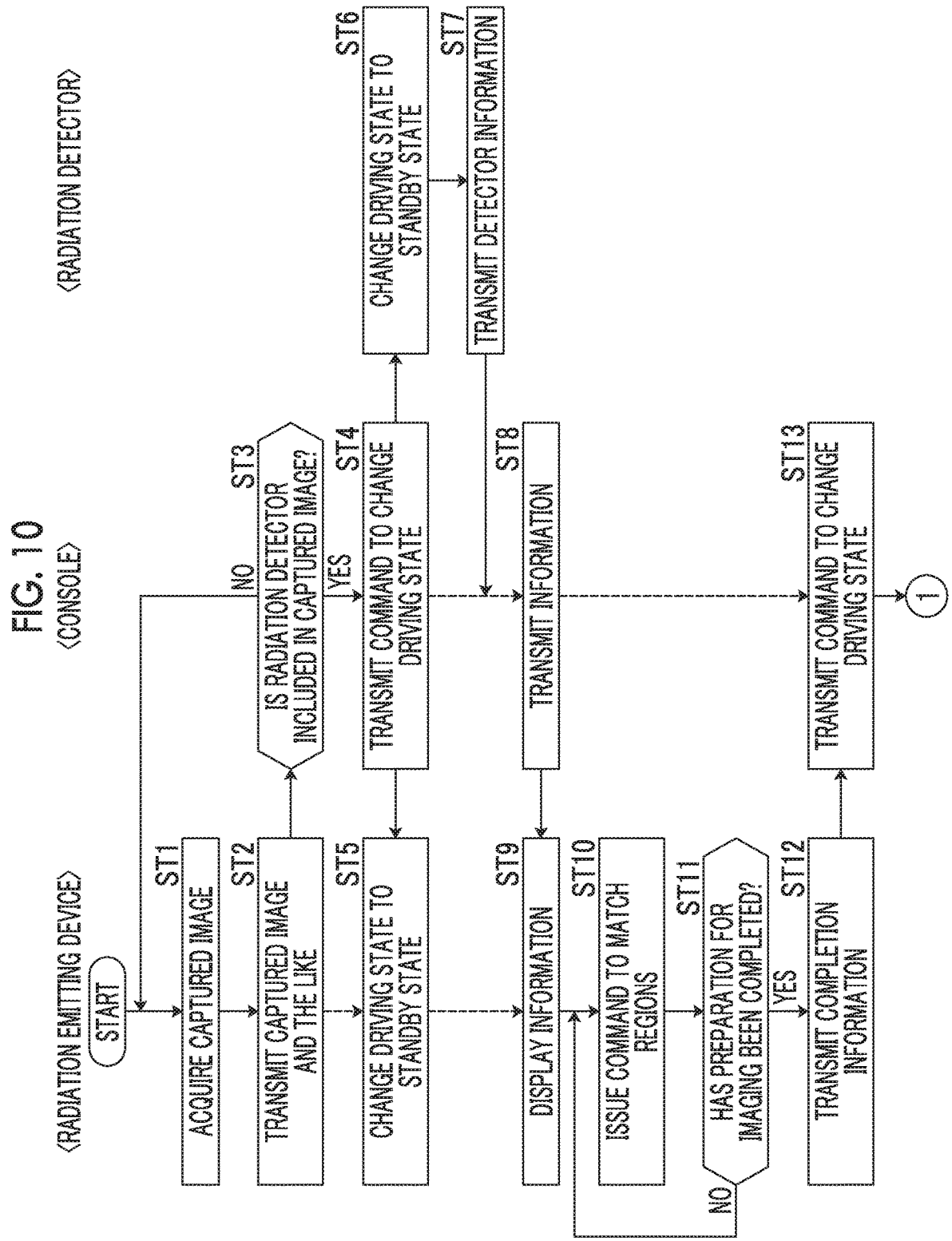
FIG. 10 is a flowchart illustrating a process performed in this embodiment.
Figure 11:
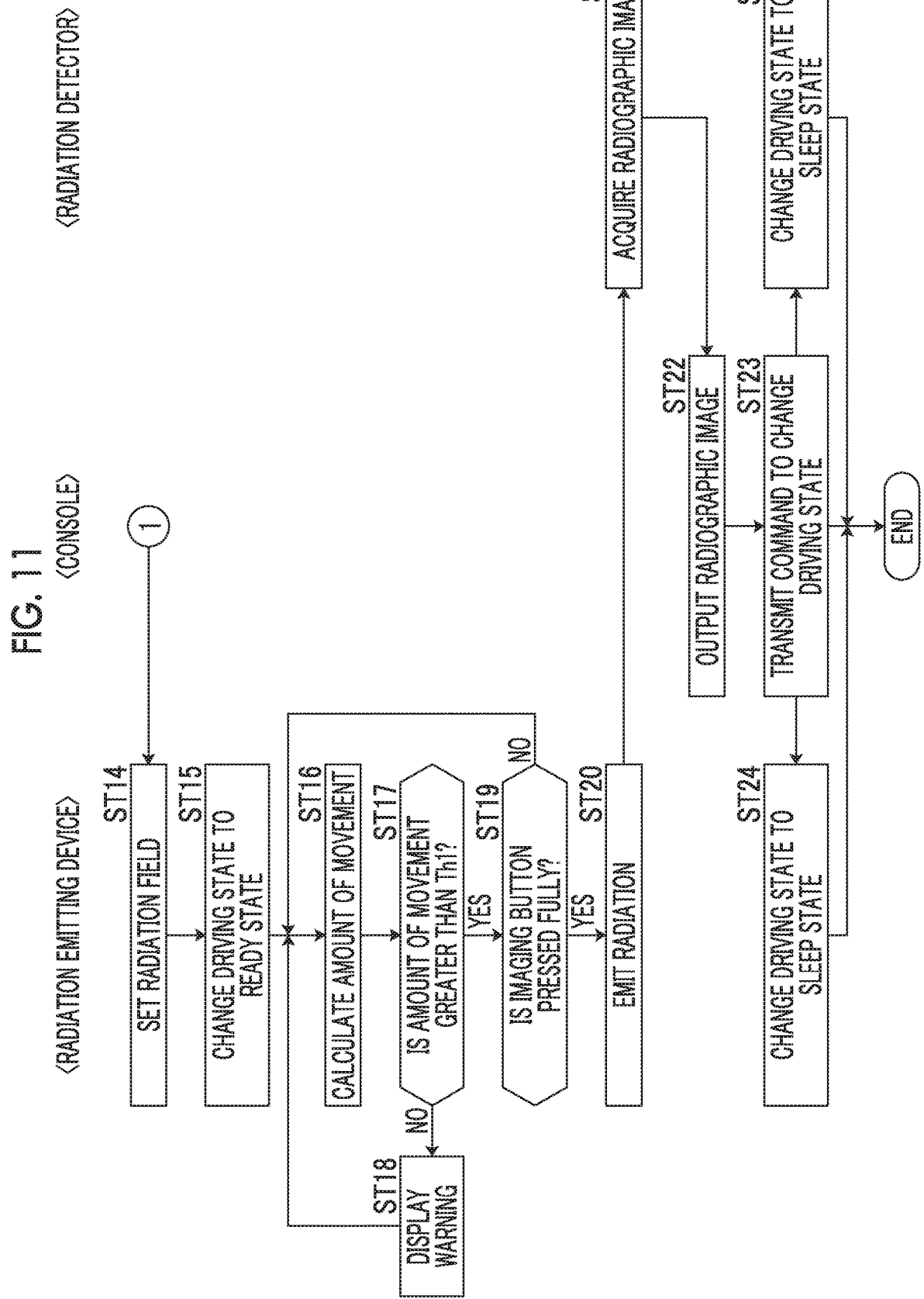
FIG. 11 is a flowchart illustrating a process performed in this embodiment.

Next, a process performed in this embodiment will be described. FIGS. 10 and 11 are flowcharts illustrating the process performed in this embodiment. It is assumed that each of the radiation emitting device 10 and the radiation detector 30 is turned on and is in the sleep state. In addition, in the radiography apparatus according to this embodiment, it is assumed that two operators handle the radiation emitting device 10 and the radiation detector 30 to perform a pre-imaging operation for positioning the radiation detector 30 behind the subject H or setting the radiation field and perform an imaging operation after the pre-imaging operation is completed. In addition, one operator may perform the same operation as described above. Information indicating the movement of the radiation detector 30 detected by the motion sensor 38 is transmitted from the radiation detector 30 in the sleep state to the console 50. Furthermore, it is assumed that the distance sensor 27 detects the SID and the SOD before imaging. First, the radiation emitting device 10 is placed above the subject H, the camera 13 captures an image of the subject H, and the captured image G1 of the subject H is acquired (Step ST1).

The radiation emitting device 10 transmits the captured image G1, the SID, the SOD, and the information of the radiation field defined by the collimator 14 to the console 50 (the transmission of, for example, the captured image: Step ST2). The driving state control unit 53 of the console 50 determines whether the captured image G1 includes the radiation detector 30 (Step ST3). In a case in which the captured image G1 does not include the radiation detector 30 as illustrated in FIG. 8, the determination result in Step ST3 is "NO" and the process returns to Step ST1. In a case in which the captured image G1 includes the radiation detector 30 as illustrated in FIG. 9, the determination result in Step ST3 is "YES" and the driving state control unit 53 transmits a command to change the driving state from the communication unit 57 to the radiation emitting device 10 and the radiation detector 30 (Step ST4).

In the radiation emitting device 10, the driving control unit 23 changes the driving state of the radiation emitting device 10 to the standby state on the basis of the command to change the driving state (Step ST5). In addition, in the radiation detector 30, the driving control unit 36 changes the driving state of the radiation detector 30 to the standby state on the basis of the command to change the driving state (Step ST6).

In the radiation detector 30, the driving control unit 36 transmits detector information including information indicating the driving state of the radiation detector 30 and remaining battery level information indicating the remaining level of the battery 39 from the communication unit 37 to the console 50 (Step ST7). The communication unit 57 of the console 50 receives the detector information. The control unit 59 acquires information related to the detector which includes the identification information of the radiation detector 30, radiation detector position information indicating the position of the radiation detector 30 on the captured image G1, information indicating the vertical direction of the radiation detector 30, and the center position information of the radiation detector 30, on the basis of any one of the markers 34A to 34D of the radiation detector 30 included in the captured image G1. In addition, the control unit 59 subtracts the SOD from the SID to calculate the body thickness of the subject H and sets imaging conditions from the body thickness.

Figure 12:
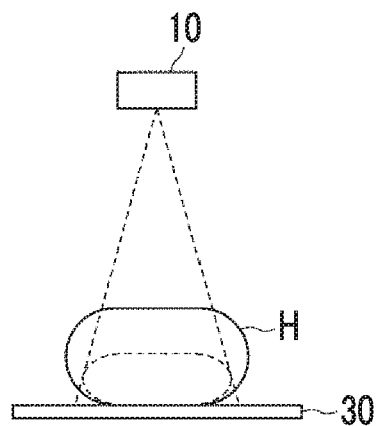
FIG. 12 is a diagram illustrating a change in a radiation field depending on the body thickness of the subject.

Here, the size of the field of the radiation emitted from the radiation emitting device 10 is different in a case in which the body thickness of the subject H is large and in a case in which the body thickness of the subject H is small, as illustrated in FIG. 12. Specifically, as the body thickness decreases, the radiation field increases. Therefore, the control unit 59 calculates the body thickness of the subject H from the SID and the SOD and acquires information related to the radiation field which includes information about the size and the position of the center of a radiation field region, on the basis of the information of the range defined by the collimator 14 which has been transmitted from the radiation emitting device 10. Then, the control unit 59 transmits, the identification information, the detector information, the information related to the detector, the information related to the radiation field, and the imaging conditions to the radiation emitting device 10 (the transmission of information: Step ST8).

In addition, the imaging conditions may be set according to a part of the subject H included in the captured image G1. Information about the part of the subject H may be input to the radiation emitting device 10 by the operator and acquired. Alternatively, the information may be input through the input unit 56 of the console 50. In addition, an appropriate quality of radiation (whether the voltage is high or low) varies depending on the type of scintillator used in the image detection unit 31 provided in the radiation detector 30. Therefore, the imaging conditions may be set according to the material forming the scintillator used in the image detection unit 31 provided in the radiation detector 30, in addition to the body thickness. In this case, the storage unit 55 may store a table in which the information of the scintillator used in the image detection unit 31 and the imaging conditions, which correspond to the identification information of the radiation detector 30, are associated with each other. In this case, it is possible to set the imaging conditions corresponding to the identification information of the radiation detector 30 acquired from the captured image G1 with reference to the table. In addition, in a case in which imaging information obtained. when an image of the same subject H is captured using the same radiation emitting device 10 and the same radiation detector 30 has been stored, the imaging conditions may be set, considering the imaging information.

Here, in a case in which the radiation detector 30 is moved after the radiation detector 30 is included in the captured image G1, the radiation detector 30 is moved to a position out of the angle of view of the camera 13 and the radiation detector 30 may not be included in the captured image G1. In addition, in a case in which the radiation detector 30 is completely hidden by the subject H, the radiation detector is not included in the captured image G1. In this case, since the markers 34A to 34D are not included in the captured image G1, it is difficult to specify, for example, the position of the radiation detector 30 from only the captured image G1.

Therefore, in this embodiment, in a case in which the radiation detector 30 is not included in the captured image G1, the control unit 59 acquires the movement information of the radiation detector 30 detected by the motion sensor 38. Then, the control unit 59 calculates the amount of movement of the radiation detector 30 from a reference position which is the position of any one of the markers 34A to 34D of the radiation detector 30 in a case in which any one of the markers 34A to 34D of the radiation detector 30 is included in the captured image G1, on the basis of the movement information and the size of the detection region of the radiation detector 30. Then, the control unit 59 acquires radiation detector position information on the basis of the calculated amount of movement. In this way, even in a case in which the radiation detector 30 is not included in the captured image G1, it is possible to track the position of the radiation detector 30.

The driving control unit 23 of the radiation emitting device 10 displays the identification information of the radiation detector 30, the driving state of the radiation detector 30, the vertical direction of the radiation detector 30, the remaining battery level of the radiation detector 30, the region corresponding to the radiation detector 30, the position of the center of the radiation detector 30, and the radiation field defined by the collimator 14 so as to be superimposed on the captured image G1 displayed on the monitor 15, on the basis of the information transmitted from the console 50 (the display of information: Step ST9).

Figure 13:
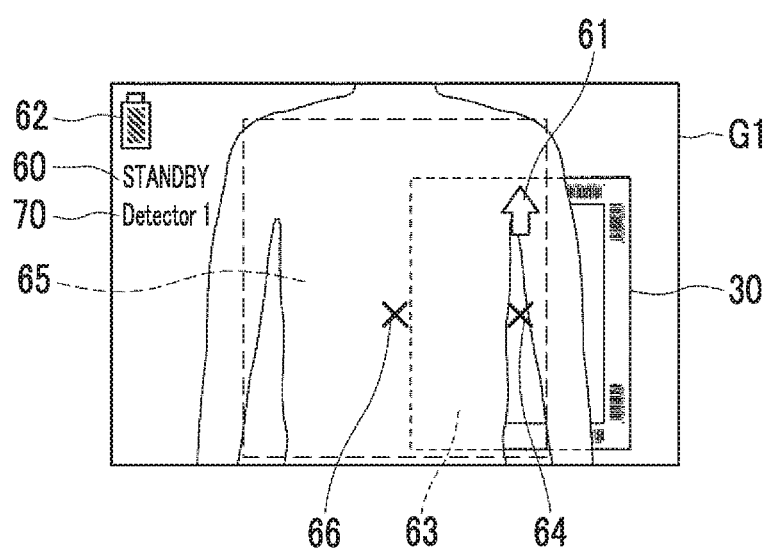
FIG. 13 is a diagram illustrating a captured image on which various kinds of information are superimposed.

FIG. 13 is a diagram illustrating the captured image G1 on which various kinds of information are superimposed. As illustrated in FIG. 13, a text (here, "standby") 60 indicating the driving state of the radiation detector 30, an arrow 61 indicating the vertical direction of the radiation detector 30, an icon 62 indicating the remaining battery level of the radiation detector 30, a detection region 63 corresponding to the detection region of the radiation detector 30, a center position 64 of the radiation detector 30, a radiation field region 65, a center position 66 of the radiation field region 65, and a text 70 "Detector1" which is the identification information of the radiation detector 30 are displayed on the captured image G1 displayed on the monitor 15 so as to be superimposed thereon. In addition, the center position 66 of the radiation field is displayed in the radiation field region 65. It is preferable that the detection region 63 and the radiation field region 65 are displayed so as to be distinguished from each other. For example, it is preferable that the color of the detection region 63 is different from the color of the radiation field region 65. The colors may be designated by a command from the console 50.

In the console 50, it is preferable that the control unit 59 detects the color of the clothes of the subject H from the captured image G1 and designates the colors of the detection region 63 and the radiation field region 65 so as to be different from the color of the clothes. In this case, it is possible to prevent the confusion between the color of the clothes of the subject H and the colors of the detection region 63 and the radiation field region 65 superimposed on the captured image G1.

Figure 14:
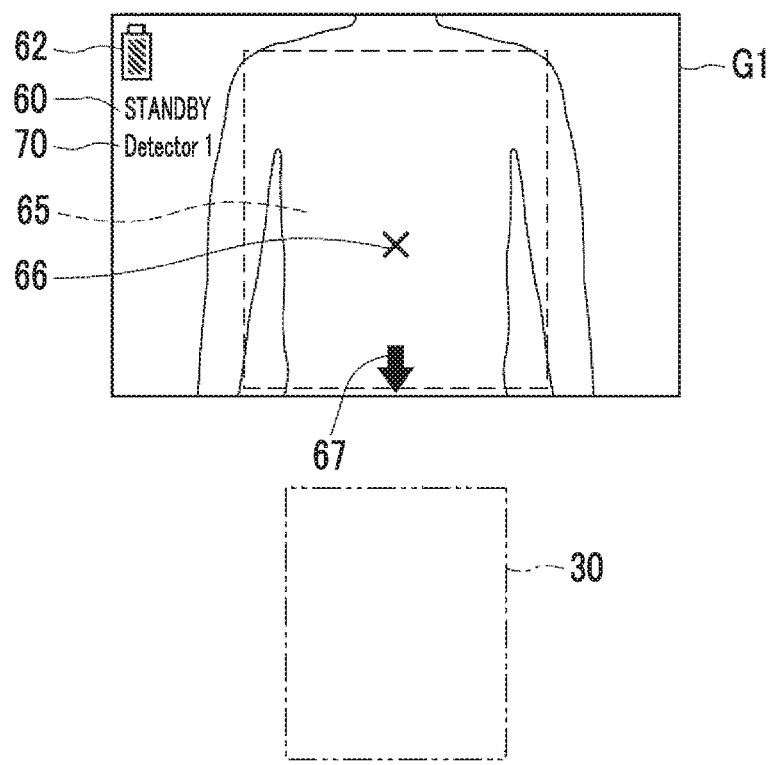
FIG. 14 is a diagram illustrating a captured image on which information indicating a direction in which the radiation detector is present is superimposed.

In a case in which the radiation detector 30 is included in the captured image G1 and then the radiation detector 30 is excluded from the captured image G1, information indicating the direction in which the radiation detector 30 is present may be displayed in the captured image G1, using the radiation detector position information calculated on the basis of the movement information of the radiation detector 30. FIG. 14 is a diagram illustrating a captured image on which the information indicating the direction in which the radiation detector 30 is present is superimposed, in addition to various kinds of information. In FIG. 14, the position of the radiation detector 30 is represented by a virtual line. As illustrated in FIG. 14, in addition to the information superimposed on the captured image G1 illustrated in FIG. 13, an arrow 67 as information indicating the direction in which the radiation detector 30 is present is displayed on the captured image G1 displayed on the monitor 15. In addition, instead of the arrow 67, letters indicating, for example, the up, down, left, and right sides may be used as the information indicating the direction in which the radiation detector 30 is present. Even in a case in which the radiation detector 30 is completely hidden behind the subject H, it is possible to specify the position of the radiation detector 30 in the captured image G1, using the radiation detector position information calculated on the basis of the movement information of the radiation detector 30. Therefore, it is possible to display the detection region 63 on the captured image G1.

Figure 15:
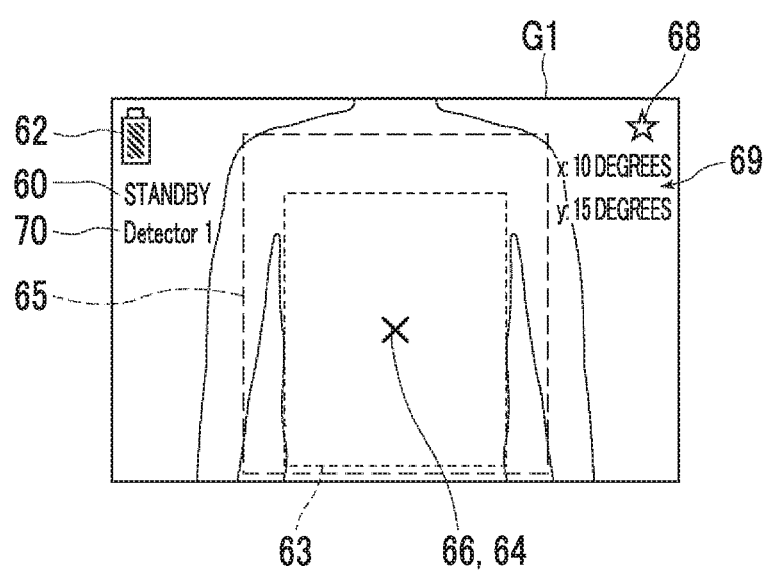
FIG. 15 is a diagram illustrating a state in which the position of the center of a radiation field region is matched with the position of the center of a detection region.

The operators of the radiation emitting device 10 and the radiation detector 30 perform a pre-imaging operation in cooperation with each other. That is, the operator of the radiation detector 30 moves the radiation detector 30 to an appropriate position behind the subject H and the operator of the radiation emitting device 10 checks whether the radiation detector 30 has been moved to an appropriate position while seeing the image displayed on the monitor 15. In addition, the operator moves the position of the radiation emitting device 10 if necessary. As illustrated in FIG. 15, the center position 66 of the radiation field region 65 and the center position 64 of the detection region 63 can be aligned with each other by this operation.

Furthermore, the control unit 59 may determine whether the center position of the radiation detector 30 has been aligned with the center position 66 of the radiation field region 65. In a case in which the positions have been aligned with each other, the control unit 59 may transmit information indicating the alignment to the radiation emitting device 10. In a case in which the information indicating the alignment is received, the radiation emitting device 10 displays information indicating that the center positions have been aligned with each other, such as a text "the center positions have been aligned with each other" or a mark indicating that the center positions have been aligned with each other, on the monitor 15. In FIG. 15, a star-shaped mark 68 indicates that the center positions have been aligned with each other. In addition, instead of displaying the text or the mark on the monitor 15, any method may be used as long as it can inform the operator that the center position of the radiation detector 30 has been aligned with the center position 66 of the radiation field region 65. For example, a method that outputs sounds or a method that blinks the monitor 15 may be used.

In a case in which the center position of the radiation detector 30 has been aligned with the center position 66 of the radiation field region 65, information about the tilt of the radiation detector 30 with respect to the radiation emitting device 10 may be displayed so as to be superimposed on the captured image G1, on the basis of the information about the tilt of the radiation detector 30 included in the movement information of the radiation detector 30. Here, the tilt of the radiation detector 30 with respect to the radiation emitting device 10 means a two-dimensional tilt with respect to the plane perpendicular to a radiation emission optical axis. In a case in which the x-axis and the y-axis are set on the plane of the radiation detector 30, the tilt is a tilt angle about each of the x-axis and the y-axis. In a case in which the center position of the radiation detector 30 has been aligned with the radiation emission axis, the control unit 59 of the console 50 acquires information about the tilt of the radiation detector 30 and transmits the information to the radiation emitting device 10. In a case in which the information about the tilt of the radiation detector 30 is received, the radiation emitting device 10 displays the angles about the x-axis and the y-axis on the monitor 15. FIG. 15 illustrates angle information 69 indicating the angles about the x-axis and the y-axis. In this way, the operator can adjust the tilt of the radiation detector 30 such that the angles of the radiation detector 30 about the x-axis and the y-axis are 0 and the radiation emission axis is perpendicular to the radiation detector 30.

In addition, the control unit 59 may calculate the relative tilt between the radiation emitting device 10 and the radiation detector 30, using the movement information of the radiation emitting device 10, and may transmit the calculated relative tilt to the radiation emitting device 10. In this case, after the radiation detector 30 is fixed, the tilt of the radiation emitting device 10 can be adjusted to adjust the relative tilt of the radiation detector 30 with respect to the radiation emitting device 10. In a case in which the radiation emission axis is perpendicular to the radiation detector 30, the color of the detection region 63 superimposed on the captured image G1 may be changed or the detection region 63 may be blinked. In this case, the operator can easily recognize that the radiation emission axis has been perpendicular to the radiation detector 30.

Here, in the state illustrated in FIG. 15, since the radiation field region 65 is larger than the detection region 63, it is difficult to convert a radiation component which has not been emitted to the radiation detector 30 among radiation components transmitted through the subject H into an image and the radiation component is unnecessary. In addition, the irradiation of the subject H with the unnecessary radiation component causes an increase in the amount of radiation emitted to the subject H.

Figure 16:
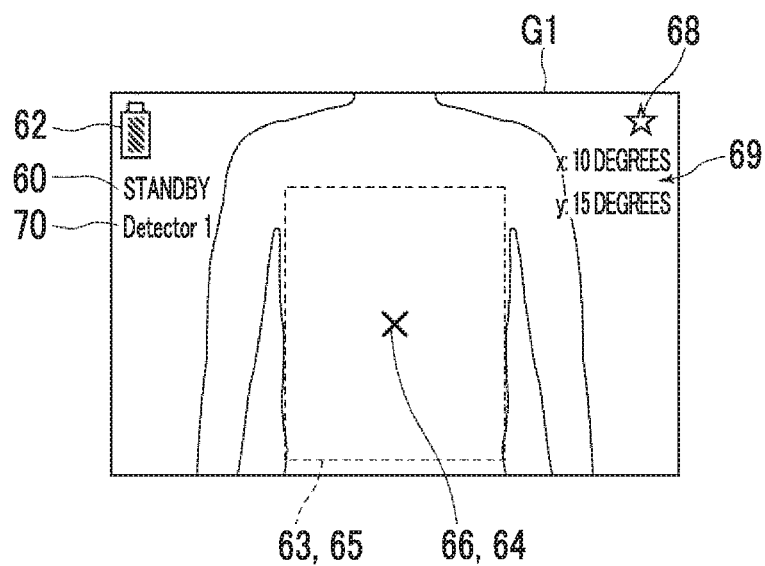
FIG. 16 is a diagram illustrating a state in which the radiation field region is matched with e detection region.

For this reason, the operator of the radiation emitting device 10 inputs a command to match the radiation field region 65 with the detection region 63, using the input unit 24 (the instruction of the matching between the regions: Step ST10). The command to match the regions is a command that is input by the operation of the radiation field region 65 displayed on the monitor 15 by, for example, the finger of the operator to match the radiation field region 65 with the detection region 63, as illustrated in FIG. 16. The collimator control unit 21 may drive the collimator 14 in operative association with the command to match the regions. In a case in which the collimator control unit 21 drives the collimator 14 whenever the command to match the radiation field region 65 with the detection region 63 is issued, power consumption increases. For this reason, in this embodiment, the collimator control unit 21 may drive the collimator 14 in a case in which the issuing of the command to match the radiation field region 65 with the detection region 63 through the input unit 24 ends and the input unit 24 receives input information indicating that preparation for imaging has been completed.

Therefore, the driving control unit 23 of the radiation emitting device 10 determines whether the preparation for imaging has been completed (Step ST11). As described above, information indicating that the preparation for imaging has been completed may be received from the input unit 24. The radiation field lamp 29 is turned on by a first-stage operation of pressing the imaging button 18 halfway and radiation is emitted by a second-stage operation of pressing the imaging button 18 fully. Therefore, the information indicating that the preparation for imaging has been completed may be received by the operation of pressing the imaging button 18 halfway. In this embodiment, it is assumed that the information indicating that the preparation for imaging has been completed is received by the operation of pressing the imaging button 18 halfway. In a case in which the determination result in Step ST11 is "NO", the process returns to Step ST10.

In a case in which the determination result in Step ST11 is "YES", the driving control unit 23 turns on the radiation field lamp 29 to transmit completion information indicating that the preparation for imaging has been completed to the console 50 (Step ST12). In a case in which the driving state control unit 53 of the console 50 receives the completion information, the driving state control unit 53 transmits a command to change the driving state of the radiation emitting device 10 to the ready state to the radiation emitting device 10 (Step ST13). Then, the driving control unit 23 of the radiation emitting device 10 directs the collimator control unit 21 to drive the collimator 14 such that the radiation field is set (Step ST14). At that time, it is preferable to notify the operator that the collimator 14 is being driven by, for example, blinking the radiation field region 65 displayed on the monitor 15. Here, the number of times the radiation field region 65 blinks per second may be equal to or less than 10, for example, about 2 to 5. The driving control unit 23 of the radiation emitting device 10 does not receive the operation of the imaging button 18 while the collimator 14 is being driven. Then, in a case in which the driving of the collimator 14 is completed, the driving control unit 23 turns off the radiation field lamp 29 and changes the driving state of the radiation emitting device 10 to the ready state (Step ST15).

In addition, the driving control unit 23 detects the movement of the radiation emitting device 10, using the motion sensor 28, and calculates the amount of movement of the radiation emitting device 10 per unit time (Step ST16). The amount of movement of the radiation emitting device 10 per unit time corresponds to the shaking of the hand of the operator. The driving control unit 23 determines whether the amount of movement per unit time is less than a threshold value Th1 (Step ST17). In a case in which the determination result in Step ST17 is "NO", the driving control unit 23 displays a warning on the monitor 15 (Step ST18) and returns to Step ST16. For example, the operator can take an action of firmly holding the radiation emitting device 10 in response to the displayed warning.

In a case in which the determination result in Step ST17 is "NO", the driving control unit 23 controls the radiation source 19 such that radiation is not emitted even in a case in which the imaging button 18 is operated. Instead of this configuration, for example, the imaging button 18 may be locked such that the imaging button 18 is not operable. In addition, the threshold value Th1 may change depending on the radiation emission time included in the imaging conditions. For example, in a case in which the radiation emission time is long, the influence of hand shaking increases. Therefore, the threshold value Th1 may be changed such that it decreases as the radiation emission time increases.

In a case in which the determination result in Step ST17 is "YES", the driving control unit 23 further determines whether the imaging button 18 has been pressed fully (Step ST19). In a case in which the determination result in Step ST19 is "NO", the process returns to Step ST16. In a case in which the determination result in Step ST19 is "YES", the driving control unit 23 drives the radiation source 19 such that radiation is emitted to the subject H and the subject H is irradiated with the radiation (Step ST20). In a case in which the determination result in Step ST17 is "YES", the driving control unit 23 may display information indicating that imaging can be performed on the monitor 15. In a case in which the determination result in Step ST17 changes from "NO" to "YES", the driving control unit 23 stops the display of the warning on the monitor 15 such that the radiation source 19 can be driven by the operation of the imaging button 18. In addition, in a case in which the imaging button 18 is locked such that it is not operable, for example, the imaging button 18 is unlocked so as to be operable. Here, the completion of the emission of radiation may be notified by, for example, sounds.

The radiation detector 30 detects the radiation transmitted through the subject H and acquires the radiographic image G2 of the subject H (Step ST21). The acquired radiographic image G2 is transmitted to the console 50 and the image processing unit 52 performs image processing for improving image quality and outputs the radiographic image G2 to the output unit 54 (Step ST22). The radiographic image G2 subjected to the image processing may be transmitted to the radiation emitting device 10 and the captured image G1 and the radiographic image G2 may be displayed on the monitor 15 so as to be superimposed on each other or only the radiographic image G2 may be displayed. In this case, it is possible to determine whether the radiographic image G2 has been appropriately acquired.

In a case in which the radiographic image G2 is acquired, the control unit 59 of the console 50 transmits a command to change the driving state of the radiation emitting device 10 and the radiation detector 30 to the sleep state to the radiation emitting device 10 and the radiation detector 30 (Step ST23). Then, each of the radiation emitting device 10 and the radiation detector 30 changes the driving state to the sleep state (Steps ST24 and ST25) and the process ends.

As such, in this embodiment, the driving state of at least one of the radiation emitting device 10 or the radiation detector 30 is controlled on the basis of whether the radiation detector 30 is included in the captured image G1. Here, in a state in which the radiation detector 30 is not included in the captured image G1, an image of the subject H is not captured. After the radiation detector 30 is included in the captured image G1, radiation is emitted to the subject H to capture an image of the subject H. Therefore, the configuration in which the driving state of at least one of the radiation emitting device 10 or the radiation detector 30 is controlled on the basis of whether the radiation detector 30 is included in the captured image G1 makes it possible to prevent at least one of the radiation emitting device 10 or the radiation detector 30 from being changed to the driving state in which power consumption is large in a situation in which imaging is not immediately performed. Therefore, it is possible to reduce the power consumption of the radiography apparatus 1 according to this embodiment.

In the above-described embodiment, the radiation detector 30 is turned on in a case in which it starts to be used on each day of use and is changed to the sleep state. In a case in which the radiation detector 30 is detected from the captured image G1, the driving state of the radiation detector 30 is changed from the sleep state to the standby state. However, in a case in which the radiation detector 30 is in an off state and is detected from the captured image G1, the driving state of the radiation detector 30 may be changed from a power-off state to a power-on state, for example, any one of the sleep state, the standby state, and the ready state. In this case, the radiation detector 30 has, for example, a wireless communication function, such as a near field communication function and a control device that is driven independently of the radiation detector 30 and has a function of turning on the radiation detector 30 is provided. Then, the console 50 communicates with the control device. In a case in which the radiation detector 30 is detected from the captured image G1, the console 50 transmits a command to change the driving state to the control device. Then, the control device drives the driving control unit 23 of the radiation detector 30 to turn on the radiation detector 30. As such, in a case in which the radiation detector 30 is detected from the captured image G1, the driving state of the radiation detector 30 is changed from the power-off state to the power-on state, which makes it possible to reduce the power consumption of the radiation detector 30 almost to zero until a pre-imaging operation is performed. Therefore, it is possible to further reduce the power consumption of the radiography apparatus 1 according to this embodiment.

Figure 17:
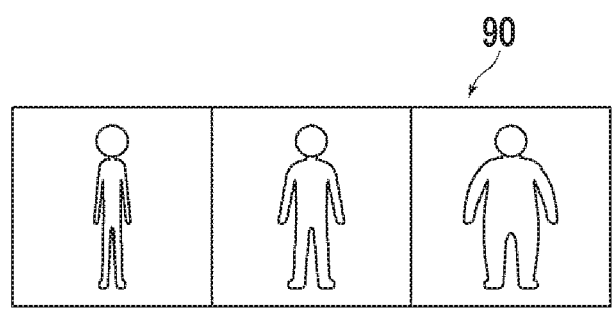
FIG. 17 is a diagram illustrating icons indicating, for example, a thin person, a normal person, and a fat person.

In the above-described embodiment, the distance sensor 27 detects the SID and the SOD and the body thickness of the subject H is calculated from the SID and the SOD. However, in the radiation emitting device 10, the operator may input the body thickness of the subject H using the input unit 24. In this case, the measured body thickness of the subject H may be input. As illustrated in FIG. 17, icons 90 indicating a thin person, a normal person, and a fat person may be displayed on the monitor 15 such that the operator selects any one of the displayed icons 90 to input the body thickness.

Since the radiation emitting device 10 according to this embodiment is portable, the radiation emitting device 10 may emit radiation to the direction in which the subject H is absent. In order to prevent this situation, it is preferable that the driving control unit 23 controls the radiation source 19 such that radiation is not capable of being emitted in a state in which an object required for imaging, such as the radiation detector 30, is not included in the captured image G1.

In the above-described embodiment, the distance sensor 27 measures the SID and the SOD before a pre-imaging operation starts. However, the distance sensor 27 may measure the SID and the SOD during the pre-imaging operation. In this case, a position where the SID and the SOD are measured may be designated on the monitor 15 and the information of the position may be transmitted to the console 50. In this case, it is possible to recognize the position where the body thickness is acquired in the subject H in the console 50.

In the above-described embodiment, the control unit 59 of the console 50 sets the imaging conditions. However, the control unit 59 may determine whether radiation can be emitted according to the set imaging conditions, on the basis of information about the remaining level of the battery 26 in the radiation emitting device 10. In a case in which radiation is not capable of being emitted according to the set imaging conditions, information indicating that radiation is not capable of being emitted may be transmitted to the radiation emitting device 10. The radiation emitting device 10 may display the information indicating that imaging is not available on the monitor 15 such that the operator can recognize that the remaining level of the battery 26 is insufficient. Therefore, the operator can take, for example, an action of replacing the battery 26 or an action of preparing another radiation emitting device 10.

In the above-described embodiment, the console 50 may transmit, for example, the captured image G1, the identification information of the radiation detector 30, the radiation detector position information, the information indicating the vertical direction, the center position information, the information indicating the driving state of the radiation detector 30, and the remaining battery level information to the terminal 80 and various kinds of information may be displayed on the terminal 80 so as to be superimposed on the captured image G1, as in the monitor 15. In this case, for example, a doctor can monitor the state of an operation before an image of the subject H is captured in the terminal 80 of the doctor.

In the above-described embodiment, the vertical direction of the radiation detector 30 is the left-right direction of the captured image G1. In some cases, the top and bottom of the radiation detector 30 are opposite to the top and bottom of the captured image G1. In this case, the top and bottom of the acquired radiographic image G2 are not matched with the top and bottom of the captured image G1. Therefore, in a case in which the acquired radiographic image G2 is displayed without any change, it is difficult to see the radiographic image G2. In this embodiment, the console 50 detects the vertical direction of the radiation detector 30. Therefore, it is possible to rotate the displayed radiographic image G2 such that the top and bottom of the radiographic image G2 are correct. As such, the radiographic image G2 is rotated such that the top and bottom of the radiographic image G2 are correct to match the top and bottom of the radiographic image G2 with the top and bottom of the captured image G1. Therefore, it is possible to easily see the displayed radiographic image G2.

In the above-described embodiment, in some cases, the amount of movement of the radiation emitting device 10 per unit time is equal to or greater than the threshold value Th1 while radiation is being emitted. In this case, the emission of radiation may be temporarily stopped and radiation may be emitted for the remaining radiation emission time in a case in which the amount of movement of the radiation emitting device 10 per unit time is less than the threshold value Th1. In this case, two radiographic images are acquired before and after the emission of radiation is stopped. The console 50 may combine the two radiographic images using, for example, an addition process to generate a final radiographic image G2.

In the above-described embodiment, the driving state of both the radiation emitting device 10 and the radiation detector 30 is controlled on the basis of whether the radiation detector 30 is included in the captured image G1. However, the driving state of only the radiation emitting device 10 may be controlled or the driving state of only the radiation detector 30 may be controlled.

In the above-described embodiment, the console 50 may transmit the generated radiographic image G2 to the radiation emitting device 10. Then, the radiation emitting device 10 may display the radiographic image G2 on the monitor 15 such that the operator checks whether imaging has succeeded. In this case, the captured image G1 and the radiographic image G2 may be displayed side by side or may be displayed such that the radiographic image G2 is superimposed on the captured image G1.

In the above-described embodiment, the imaging button 18 is pressed halfway to turn on the radiation field lamp 29. However, the turn-on and turn-off of the radiation field lamp 29 may be switched. For example, in a case in which the radiographic image G2 of the face of an animal is acquired, it is necessary to irradiate the face of the animal with radiation. In this case, when the radiation field lamp 29 is turned on, light is emitted to the face of the animal and the animal is likely to become wild. For this reason, the control unit 59 of the console 50 may determine a part of the subject H included in the captured image G1. In a case in which the part is the face of the animal, the control unit 59 may instruct the radiation emitting device 10 not to turn on the radiation field lamp 29 even when the imaging button 18 is pressed halfway. The driving control unit 23 of the radiation emitting device 10 does not turn on the radiation field lamp 29 and maintains the radiation field lamp 29 in an off state even in a case in which the imaging button 18 is pressed halfway, in response to the instruction. In this way, it is possible to prevent the animal from becoming wild due to visible light emitted from the radiation field lamp 29. Since the operator knows the part of the subject H, the turn-on and turn-off of the radiation field lamp 29 may be switched by a command input by the operator through the input unit 24.

In the above-described embodiment, the lighting state of the radiation field lamp 29 may be changed according to the driving state of the radiation emitting device 10 and the radiation detector 30. For example, the color of the radiation field lamp 29 may be changed according to the driving state of the radiation emitting device 10 and the radiation detector 30. In this case, in Step ST5 of the flowchart illustrated in FIG. 10, the driving state of the radiation emitting device 10 is changed from the sleep state to the standby state. In a case in which the driving state of the radiation detector 30 is changed from the sleep state to the standby state in Step ST6, the driving control unit 23 of the radiation emitting device 10 turns on the radiation field lamp 29 in a predetermined color, for example, yellow for a predetermined period of time. The predetermined period of time may be, for example, 1 second or less. The operator can recognize that the driving state of the radiation emitting device 10 has been changed to the standby state and the driving state of the radiation detector 30 has been changed to the standby state, without checking the display of the monitor 15. Therefore, it is possible to rapidly perform an imaging operation.

In addition, the control unit 59 of the console 50 may determine whether the identification information of the radiation detector 30 is wrong, whether the vertical direction of the radiation detector 30 is wrong, whether the remaining battery level of the radiation detector 30 is sufficient to perform imaging, and whether the remaining battery level of the radiation emitting device 10 is sufficient to perform imaging. In a case in which the determination results are "YES", the control unit 59 may transmit information indicating the determination results to the radiation emitting device 10. In this case, the driving control unit 23 of the radiation emitting device 10 turns on the radiation field lamp in a predetermined color, for example, blue for a predetermined period of time. Then, the operator can recognize that the radiation emitting device 10 and the radiation detector 30 are in a state in which imaging is available, without checking the display of the monitor 15. Therefore, it is possible to rapidly perform an imaging operation.

In a case in which the driving state of the radiation emitting device 10 is changed to the sleep state in Step ST24 of FIG. 11 and the driving state of the radiation detector 30 is changed to the sleep state in Step ST25, the radiation field lamp 29 may be turned on in a predetermined color, for example, red for a predetermined period of time. In this case, the operator can recognize that the driving state of the radiation emitting device 10 and the radiation detector 30 have been changed to the sleep state, without checking the display of the monitor 15. Therefore, the operator can take the radiation detector 30 out of the back side of the subject H.

Instead of changing the lighting state of the radiation field lamp 29 according to the driving state of the radiation emitting device 10 and the radiation detector 30, the lighting state of the radiation field lamp 29 may be changed according to the driving state of one of the radiation emitting device 10 and the radiation detector 30.

In addition, instead of changing the lighting state of the radiation field lamp 29 according to the driving state of the radiation emitting device 10 and the radiation detector 30, the color of the radiation field lamp 29 may be changed according to the driving state of any one of the radiation emitting device 10 and the radiation detector 30. Instead of changing the color of the radiation field lamp 29 according to the driving state, the turn-on time or a blinking pattern may be changed. In addition, the color, turn-on time, and blinking pattern of the radiation field lamp 29 may be changed in combination with each other.

As a method for changing the color of the radiation field lamp 29, the radiation field lamp 29 may include light emitting elements such as LEDs that emit light of three primary colors, that is, R, G, and B. In this case, G and R light emitting elements may be turned on to emit yellow light.

Figure 18:
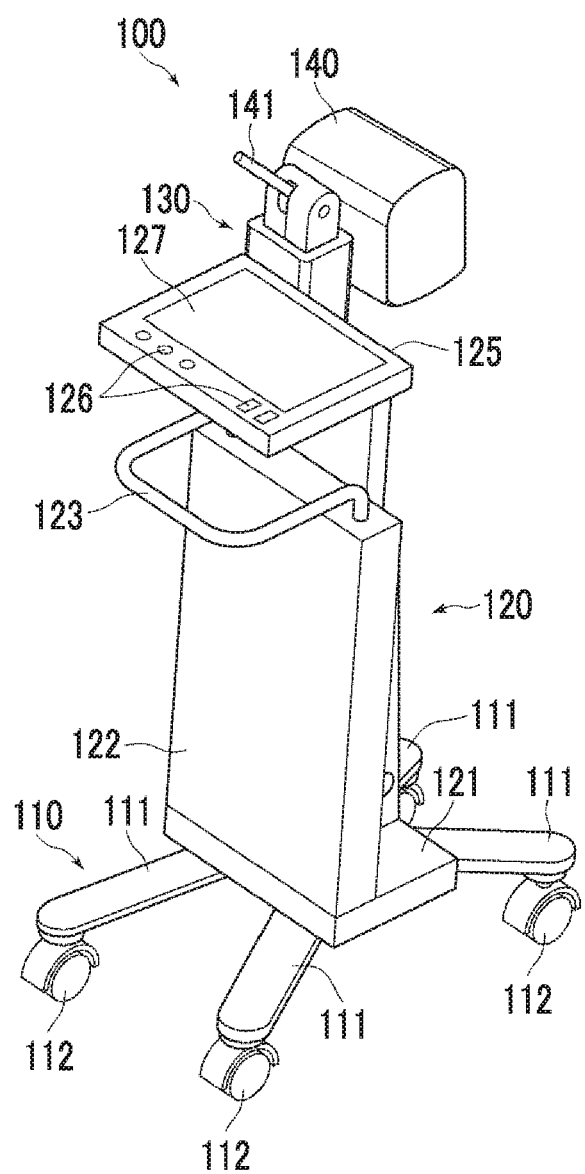
FIG. 18 is a perspective view illustrating the overall shape of a movable radiation emitting device.
Figure 19:
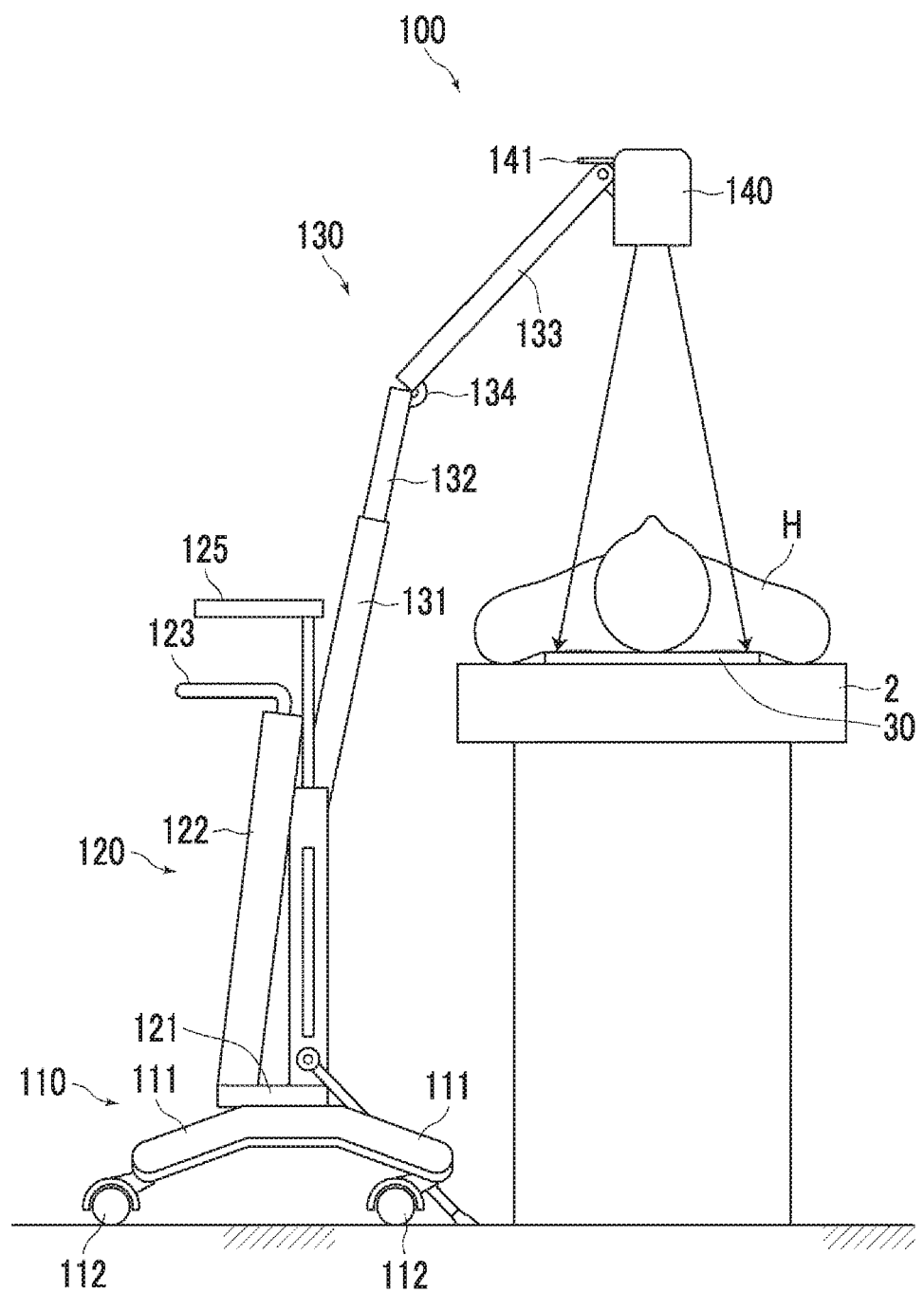
FIG. 19 is a side view illustrating the usage state of the movable radiation emitting device.

In the above-described embodiment, the portable radiation emitting device 10 is used. However, a movable radiation emitting device may be used which includes a support device that supports a radiation source unit having a radiation source. FIG. 18 is a perspective view illustrating the overall shape of a movable radiation emitting device and FIG. 19 is a diagram illustrating the usage state of the radiation emitting device. A movable radiation emitting device 100 includes a leg portion 110 that can be moved on a device mounting surface, a main body portion 120 that is held on the leg portion 110, an arm portion 130 that is connected to the main body portion 120, and a radiation source unit 140 that is attached to a leading end of the arm portion 130.

The leg portion 110 includes four legs 111 and wheel portions 112 that are attached to a lower surface of a leading end of each leg 111. The wheel portion 112 is provided with brake means (not illustrated).

In the main body portion 120, an irradiation control unit 20, a collimator control unit 21, an imaging control unit 22, a driving control unit 23, a communication unit 25, and a battery 26 which are the same as those in the radiation emitting device 10 according to the above-described embodiment are accommodated in a housing 122 that is fixed to an upper part of a base portion 121. A handle 123 for moving the radiation emitting device 100 is attached to an upper end of the housing 122. In addition, an operation unit 125 is attached to the upper part of the base portion 121.

The operation unit 125 includes, for example, an input unit 126 including operation buttons or switches for inputting signals for instructing various operations of the radiation emitting device 100 and a monitor 127 for displaying various kinds of information. In addition, the input unit 126 may be a touch panel as in the radiation emitting device 10 according to the above-described embodiment.

The arm portion 130 includes a plurality of members 131, 132, and 133 having a nesting structure. The member 132 and the member 133 are connected to each other by a rotation holding mechanism 134. The member 133 is rotated with respect to the member 132 in a direction in which the angle is changed.

The radiation source unit 140 is pivotably attached to the leading end of the member 133 of the arm portion 130. The radiation source unit 140 is provided with a camera 13, a collimator 14, a radiation source 19, a distance sensor 27, a motion sensor 28, and a radiation field lamp 29 that are the same as those in the radiation emitting device 10 according to the above-described embodiment. A locking lever 141 can be operated to fix the pivot position of the pivotable radiation source unit 140.

In the movable radiation emitting device 100, the captured image G1 of the subject acquired by the camera 13 is displayed on the monitor 127 of the operation unit 125.

In a case in which a pre-imaging operation is performed, the operator extends the arm portion 130 and sets the length of the arm portion 130 and the pivot position of the radiation source unit 140 on the upper side of the subject H such that the radiation source unit 140 is located immediately above the subject H. In this state, the camera 13 captures an image of the subject H. With this configuration, similarly to the above-described embodiment, it is possible to control the driving state of at least one of the radiation emitting device 10 or the radiation detector 30 on the basis of whether the radiation detector 30 is included in the captured image G1.

In a case in which the movable radiation emitting device 100 is used and the driving state of the device 100 is changed to the ready state, it is preferable that brake means (not illustrated) is driven to prevent the rotation of the wheel portions 112. In this case, it is possible to prevent the unexpected movement of the radiation emitting device 100 during imaging. Therefore, it is possible to prevent the blur of an acquired radiographic image.

In a case in which the movable radiation emitting device 100 is used, the expansion and contraction of the arm portion 130, the pivoting of the radiation source unit 140, and the driving of the collimator 14 may be controlled such that the detection region and the radiation field region superimposed on the radiographic image G2 are matched with each other.

In the above-described embodiment, the amount of movement of the radiation emitting device 10 per unit time is calculated using the amount of movement detected by the motion sensor 28. In this embodiment, the captured image G1 is acquired at a predetermined frame rate. Therefore, the amount of movement of the radiation emitting device 10 per unit time may be calculated on the basis of two captured images acquired at different imaging times and a difference in imaging time between the two captured images.

In the above-described embodiment, the camera 13 may be an infrared camera that can measure a temperature distribution in an imaging range using infrared rays and an infrared image indicating the temperature distribution in the imaging range may be used as the captured image G1. In this case, the captured image G1 acquired by the camera 13 indicates the temperature distribution of the surface of the subject H and the surface of an object in the vicinity of the subject H. The use of the camera 13 that can acquire an infrared image as the captured image G1 makes it possible to specify the position of the subject H on the captured image G1 on the basis of the temperature distribution indicated by the captured image G1 even in a case in which the subject H is covered with, for example, a sheet in a disaster site.

It is preferable that the camera 13 is switchable between an imaging mode using visible light and an imaging mode using infrared rays. In a case in which the camera 13 that can be switched between the imaging mode using visible light and the imaging mode using infrared rays is used, first, an image of the subject H is captured using infrared rays and the captured image G1 indicating a temperature distribution is acquired. Then, the position of the radiation field is determined using the captured image G1 indicating the temperature distribution. Then, the camera 13 may be switched to the imaging mode using visible light. Then, as in the above-described embodiment, the detection region of the radiation detector 30 and the radiation field region may be displayed so as to be superimposed on the captured image G1. Then, the position of the radiation detector 30 may be determined using the captured image G1 such that the detection region of the radiation detector 30 and the radiation field region are matched with each other. With this configuration, even in a case in which the subject H is covered with, for example, a sheet, it is possible to match the radiation field region with the detection region of the radiation detector 30 and to acquire the radiographic image G2.

As such, the captured image G1 which is an infrared image is displayed on the monitor 15 such that the operator can recognize abnormality in the body temperature of the subject H. In addition, the captured radiographic image G2 and the captured image G1 which is an infrared image may be displayed side by side on the monitor 15. In this case, the infrared image can be compared with the radiographic image G2.

Next, the operation and effect of the embodiment of the invention will be described.

Since the captured image is displayed, it is possible to check the state of the subject subjected to an imaging operation from the captured image.

At least one of the identification information of the radiation detector, the driving state of the radiation detector, the vertical direction of the radiation detector, the remaining battery level of the radiation detector, the position of the center of the radiation detector in a case in which the radiation detector is included in the captured image, or the direction in which the radiation detector is present in a case in which the radiation detector is not included in the captured image is displayed so as to be superimposed on the captured image. Therefore, it is possible to easily check these information items.

The captured image is displayed such that a region corresponding to the radiation field can be identified according to the driving state of at least one of the radiation emitting device or the radiation detector. Therefore, it is possible to display the radiation field so as to be superimposed in a situation immediately before an imaging operation with high power consumption is performed. Therefore, it is possible to easily recognize irradiation at the time of imaging in a situation immediately before an imaging operation.

The radiation field is changed in response to a decision on the issuing of a command to change the radiation field. Therefore, power consumption can be less than that in a case in which the radiation field is changed whenever the change command is issued.

The driving state of at least one of the radiation emitting device or the radiation detector is changed to a state in which imaging is available by the operation of changing the radiation field. Therefore, it is possible to change the radiation emitting device and the radiation detector to the state in which imaging is available immediately after imaging is prepared.

The visible light source is switched between an on state and an off state by an imaging operation. It is possible to turn off the visible light source in a case in which the visible light source is unnecessary.

The visible light source is switched between the on state and the off state according to an imaging part of the subject. Therefore, for example, in a case in which an image of the face of an animal is captured, it is possible to prevent the animal from becoming wild due to light emitted from the visible light source in an on state.

The lighting state of the visible light source is changed according to the driving state of at least one of the radiation emitting device or the radiation detector. Therefore, the operator can easily recognize the driving state of at least one of the radiation emitting device or the radiation detector.

In a case in which the amount of movement of the radiation emitting device per unit time is less than the threshold value, the emission of radiation from the radiation emitting device is allowed. Therefore, it is possible to prevent the blur of the acquired radiographic image due to the movement of the radiation source.

What is claimed is:

1. A radiography apparatus comprising:
   a radiation emitting device that irradiates a subject with radiation;
   a camera for capturing an image of the subject to acquire a captured image of the subject;
   a radiation detector that detects the radiation transmitted through the subject and generates a radiographic image of the subject; and
   at least one processor configured to operate as:
   a driving state control unit for controlling a driving state of at least one of the radiation emitting device or the radiation detector on a basis of whether the radiation detector is included in the captured image.

2. The radiography apparatus according to claim 1,
   wherein, in a case in which the radiation detector is included in the captured image, the driving state control unit controls the driving state of at least one of the radiation emitting device or the radiation detector such that power consumption is more than that in a case in which the radiation detector is not included in the captured image.

3. The radiography apparatus according to claim 1,
wherein, in a case in which a state of the radiation detector changes from a state in which the radiation detector is not included in the captured image to a state in which the radiation detector is included in the captured image, the driving state control unit changes the driving state of the radiation detector from a power-off state to a power-on state.

4. The radiography apparatus according to claim 1,
wherein, in a case in which a state of the radiation detector changes from a state in which the radiation detector is not included in the captured image to a state in which the radiation detector is included in the captured image, the driving state control unit changes the driving state of the radiation detector from a sleep state to a standby state.

5. The radiography apparatus according to claim 1,
wherein, in the case in which a state of the radiation detector changes from a state in which the radiation detector is not included in the captured image to a state in which the radiation detector is included in the captured image, the driving state control unit changes the driving state of the radiation emitting device from a sleep state to a standby state.

6. The radiography apparatus according to claim 1, further comprising:
a monitor for displaying the captured image.

7. The radiography apparatus according to claim 6, wherein the at least one processor is further configured to operate as:
a display control unit for displaying at least one of identification information of the radiation detector, the driving state of the radiation detector, a vertical direction of the radiation detector, a remaining battery level of the radiation detector, a position of a center of the radiation detector in the case in which the radiation detector is included in the captured image, or a direction in which the radiation detector is present in the case in which the radiation detector is not included in the captured image so as to be superimposed on the captured image displayed on the monitor.

8. The radiography apparatus according to claim 7, wherein the at least one processor is further configured to operate as:
a radiation field control unit for controlling a field of the radiation emitted to the subject,
wherein the display control unit displays the captured image such that a region corresponding to a radiation field is identifiable, according to the driving state of at least one of the radiation emitting device or the radiation detector.

9. The radiography apparatus according to claim 8,
wherein, in a case in which the driving state of at least one of the radiation emitting device or the radiation detector is changed to a driving state in which power consumption is more than that in a state in which the radiographic image is not included in the captured image, the display control unit displays the region corresponding to the radiation field so as to be superimposed on the captured image.

10. The radiography apparatus according to claim 8,
wherein the display control unit displays the region corresponding to the radiation field with a size corresponding to a source image receptor distance and a body thickness of the subject so as to be superimposed on the captured image.

11. The radiography apparatus according to claim 8, further comprising:
a user interface for receiving a command to change at least one of a position or a size of a region corresponding to a radiation field displayed on the monitor,
wherein the radiation field control unit changes the radiation field in response to the command.

12. The radiography apparatus according to claim 11,
wherein the radiation field control unit changes the radiation field in response to a decision on issuing of the command.

13. The radiography apparatus according to claim 11,
wherein the driving state control unit changes the driving state of at least one of the radiation emitting device or the radiation detector to a driving state in which imaging is available in response to a radiation field change operation of the radiation field control unit.

14. The radiography apparatus according to claim 11,
wherein the radiation field control unit changes the radiation field such that the radiation field is matched with a range of the radiation detector.

15. The radiography apparatus according to claim 8, further comprising:
a visible light source that emits visible light to a range of the radiation field in response to an imaging operation; and
wherein the at least one processor is further configured to operate as:
a switching unit for switching a turn-on and a turn-off of the visible light source by the imaging operation.

16. The radiography apparatus according to claim 15,
wherein the switching unit switches the turn-on and the turn-off of the visible light source according to a part of the subject included in the captured image.

17. The radiography apparatus according to claim 15,
wherein the driving state control unit changes a lighting state of the visible light source according to the driving state of at least one of the radiation emitting device or the radiation detector.

18. The radiography apparatus according to claim 6,
wherein the captured image is an infrared image, and the monitor displays the infrared image and the radiographic image.

19. The radiography apparatus according to claim 1, further comprising:
a sensor for detecting an amount of movement of the radiation emitting device per unit time; and
wherein the at least one processor is further configured to operate as:
an imaging allowance unit for allowing an emission of the radiation from the radiation emitting device in a case in which the amount of movement is less than a threshold value.

20. A method for controlling a radiography apparatus comprising a radiation emitting device that irradiates a subject with radiation, a camera for capturing an image of the subject to acquire a captured image of the subject, and a radiation detector that detects the radiation transmitted through the subject and generates a radiographic image of the subject, the method comprising:
controlling a driving state of at least one of the radiation emitting device or the radiation detector on a basis of whether the radiation detector is included in the captured image.

21. A non-transitory computer-readable recording medium having stored therein a program that causes a computer to perform a method for controlling a radiography apparatus comprising a radiation emitting device that irradiates a subject with radiation, a camera for capturing an image of the subject to acquire a captured image of the subject, and a radiation detector that detects the radiation transmitted through the subject and generates a radiographic image of the subject, the program comprising:
  a procedure of controlling a driving state of at least one of the radiation emitting device or the radiation detector on a basis of whether the radiation detector is included in the captured image.

* * * * *